United States Patent [19]

Mederski et al.

[11] Patent Number: 5,476,857

[45] Date of Patent: * Dec. 19, 1995

[54] IMIDAZOPYRIDINES

[75] Inventors: Werner Mederski, Erzhausen; Dieter Dorsch, Ober-Ramstadt; Norbert Beier, Reinheim; Pierre Schelling, Mühltal; Ingeborg Lues, Darmstadt; Klaus-Otto Minck, Ober-Ramstadt; Mathias Osswald, Zwingenberg, all of Germany

[73] Assignee: Merck Patent Gesellschaft mit Beschrankter Haftung, Darmstadt, Germany

[*] Notice: The portion of the term of this patent subsequent to Feb. 14, 2012, has been disclaimed.

[21] Appl. No.: 77,592

[22] Filed: Jun. 17, 1993

[30] Foreign Application Priority Data

Jun. 17, 1992 [DE] Germany .......................... 42 19 818.6
Feb. 24, 1993 [DE] Germany .......................... 43 05 602.4

[51] Int. Cl.⁶ ...................... A61K 31/44; C07D 471/04; C07D 471/06
[52] U.S. Cl. ...................... 514/303; 546/113; 546/118
[58] Field of Search ...................... 546/118, 13; 514/303

[56] References Cited

U.S. PATENT DOCUMENTS

| | | | |
|---|---|---|---|
| 4,880,804 | 11/1989 | Carini et al. | 514/234.5 |
| 5,036,048 | 7/1991 | Watkins | 514/16 |
| 5,124,335 | 6/1992 | Patchett et al. | 514/300 |
| 5,240,928 | 8/1993 | Greenlee | 514/303 |
| 5,240,938 | 8/1993 | Greenlee et al. | 514/303 |
| 5,242,928 | 9/1993 | Mederski | 514/303 |
| 5,328,911 | 7/1994 | Miyake | 514/303 |
| 5,332,744 | 7/1994 | Chakravarty | 514/261 |
| 5,389,642 | 2/1995 | Dorsch et al. | 514/303 |

FOREIGN PATENT DOCUMENTS 0400974 12/1990 European Pat. Off. .
0505893 9/1992 European Pat. Off. .

OTHER PUBLICATIONS

Chiu et al., The Journal of Pharmacology and Experimental Therapeutics, vol. 250, No. 3, pp. 867–874 (May 22, 1989).

Wong et al., The Journal of Pharmacology and Experimental Therapeutics, vol. 252, No. 2, pp. 719–725 (Oct. 26, 1989).

*Primary Examiner*—C. Warren Ivy
*Assistant Examiner*—D. Margaret M. Mach
*Attorney, Agent, or Firm*—Millen, White, Zelano, & Branigan

[57] ABSTRACT

Novel imidazopyridine derivatives of formula I:

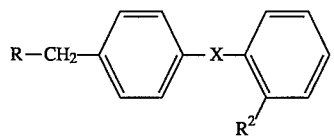

wherein
R is

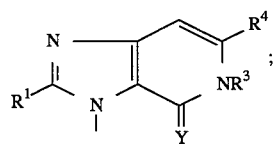

and $R^1$, $R^2$, $R^3$, $R^4$, X and Y are as defined herein, and their salts, exhibit antagonistic properties toward angiotensin II and can be used for the treatment of hypertension, aldosteronism, cardiac insufficiency and increased intraocular pressure, and of disorders of the central nervous system.

20 Claims, No Drawings

IMIDAZOPYRIDINES

SUMMARY OF THE INVENTION

The invention relates to novel imidazopyridine derivatives of formula I:

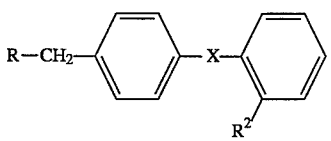

wherein
R is

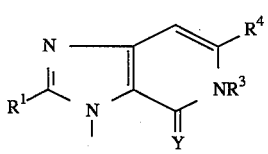

$R^1$ is A, alkenyl or alkynyl each having up to 6 C atoms, $C_3$–$C_7$—cycloalkyl—$C_kH_{2k}$— or $C_1$–$C_6$—alkyl in which a $CH_2$ group is replaced by O or S, $R^2$ is H, COOH, COOA, CN, $NO_2$, $NHCOR^5$, $NHSO_2R^5$ or 1H-tetrazol- 5-yl, $R^3$ is alkenyl having 2–6 C atoms in the "alkenyl" moiety, monosubstituted or polysubstituted by COOH, COOA, CN, $NO_2$, $NR^6R^7$, $NHCOR^8$, $NHSO_2R^8$, Hal and/or Ar, or is —$C_nH_{2n}$—$R^9$ or —$CHR^{10}$—$C_kH_{2k}$—$R^{11}$.

$R^4$ is H or Hal, $R^5$ and $R^8$ are each alkyl having 1–5 C atoms, wherein one or more H atoms can also be replaced by F, $R^6$ and $R^7$ are each H, A, alkenyl or alkynyl each having up to 6 C atoms, Ar, Ar—$C_nH_{2n}$— or $Het^2$.

$R^6$ is also —$CH_2COOA$, —$SO_2$—A or —$SO_2$—Ar, $R^6$ and $R^7$ together are also an alkylene chain having 2–5 C atoms, which can be monosubstituted or polysubstituted by carbonyl oxygen, Ar, $Het^2$, —CO—Ar, —COOA, —CO—N(A)$_2$, —$CH_2OH$, —$SO_2$—Ar and/or —NH—CO—A and/or interrupted by O or by —$NR^{16}$—, $R^9$ is cycloalkyl having 3–8 C atoms, $Het^1$, —CO—$NR^6R^7$, —CO—$R^4$, —C(=$NR^{12}$)—A, —C(=$NR^{12}$)—$Het^2$, —S(O)$_m$—A, —S(O)$_m$—Ar, —S(O)$_m$—$Het^2$, —$SO_2$—NH—$Het^2$ or —$SO_2$—$OR^{15}$, $R^{10}$ is COOH, COOA, CN, $NO_2$, $NHCOR^{11}$, $NHSO_2R^{11}$ or 1H-tetrazol-5-yl, $R^{11}$ is Ar or cycloalkyl having 3–8 C atoms, $R^{12}$ is H, OH, CN, $R^{13}$, $OR^{13}$ or OAr, $R^{13}$ is A, alkenyl or alkynyl each having up to 6 C atoms, $R^{14}$ is —NH—$CHR^{15}$—COOH, —NH—$CHR^{15}$—COOA, —$CH_2S(O)_m$—Ar, —$CH_2$—COOA, —$C_nH_{2n}$—$NO_2$, $C_nH_{2n}$—$NR^6R^7$ or —$C_nH_{2n}$—NH-COOA, $R^{15}$ is H or A, $R^{16}$ is H, A, Ar, COOA, $Het^2$ or $SO_2$—Ar, X is absent or is —NH—CO—, —CO—NH—, —O—CH(COOH)—, —NH—CH(COOH)—, —NA—CH (COOH)—, —CH=C(COOH)—, —CH=C(CN)— or —CH=C(1H-tetrazol-5-yl )—, Y is O or S, A is alkyl having 1–6 C atoms, Ar is an unsubstituted phenyl group or a phenyl group monosubstituted or disubstituted by $R^5$, $OR^5$, COOH, COOA, CN, $NO_2$, $NH_2$, $NHCOR^5$, $NHSO_2R^5$, Hal or 1H-tetrazol-5-yl, $Het^1$ is a five- or six-membered saturated heterocyclic radical having 1 to 3N, O and/or S atoms, which can be monosubstituted by carbonyl oxygen or =$NR^{12}$ and/or whose ring N atom(s) can in each case be substituted by A or Ar, $Het^2$ is an unsubstituted or substituted five- or six-membered heteroaromatic radical having 1 to 3N, O and/or S atoms, which can also be fused with a benzene or pyridine ring, Hal is F, Cl, Br or I, k is 0, 1, 2, 3 or 4, m is 0, 1 or 2, and n is 0, 1, 2, 3, 4, 5 or 6, and their salts.

Similar compounds are known from European patent application A2-0 400 974.

An object of the invention is to provide novel compounds with valuable properties, especially compounds which can be used for the preparation of drugs.

Upon further study of the specification and appended claims, further objects and advantages of this invention will become apparent to those skilled in the art.

It has been found that the compounds of formula I and their salts possess very valuable pharmacological properties coupled with a good tolerance. In particular, they exhibit antagonistic properties towards angiotensin II and can therefore be used as pharmaceutical active ingredients for the prophylaxis and/or therapy of coronary, cardiovascular and vascular disorders, in particular for the treatment of angiotensin II-dependent hypertension, aldosteronism, cardiac insufficiency and increased intraocular pressure, and of disorders of the central nervous system, also of hypertrophy and hyperplasia of the blood vessels and of the heart, angina pectoris, cardiac infarct, stroke, restenoses after angioplasty or by-pass operations, arteriosclerosis, glaucomas, macular degeneration, hyperuricaemia, kidney function disorders, e.g., kidney failures, diabetic nephropathy, diabetic retinopathy, psoriasis, angiotensin II-mediated disorders in female reproductive organs, perceptive disorders, e.g., dementia, amnesia, memory function disorders, anxiety states, depression and/or epilepsy.

These effects can be determined by conventional in vitro or in vivo methods such as, for example, those described in U.S. Pat. Nos. 4,880,804, 5,036,048 and International Patent Application 91/14367 and also by A. T. Chiu et al., J. Pharmacol. Exp. Therap. 250, 867–874 (1989), and by P. C. Wong et al., ibid. 252, 719–725 (1990; in vivo, on rats).

The invention relates to the compounds of formula I and their salts and to a process for the preparation of these compounds and their salts, characterized in that (a) a compound of formula II:

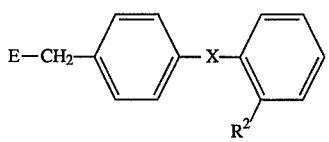 II wherein

E is Cl, Br, I, a free OH group or an OH group which has been functionally modified to acquire reactivity, and R² and X are as defined in formula I, is reacted with a compound of formula III:

H—R     III wherein

R is as defined in formula I, or (b) a compound of formula IV:

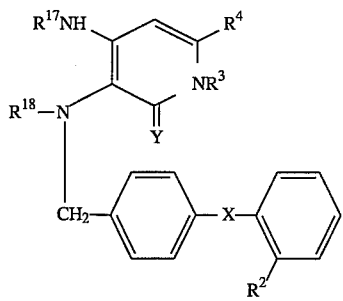 IV wherein

R¹⁷ is R¹—CO or H,

R¹⁸ is H (if R¹⁷ is R¹—CO) or R¹—CO (if R¹⁷ is H), and

R¹, R², R³, R⁴, X and Y are as defined in formula I, is treated with a cyclizing agent, or (c) to prepare a compound of formula I wherein X is —NH—CO— or —CO—NH—, a compound of formula V:

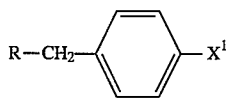 V wherein

X¹ is NH₂ or COOH, and

R is as defined in formula I, or a reactive derivative of this compound, is reacted with a compound of formula VI:

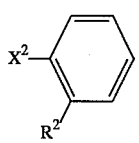 VI wherein

X² is COOH (if X¹ is NH₂) or NH₂ (if X¹ is COOH), and

R² is as defined in formula I, or with a reactive derivative of this compound, or (d) a compound of formula VII:

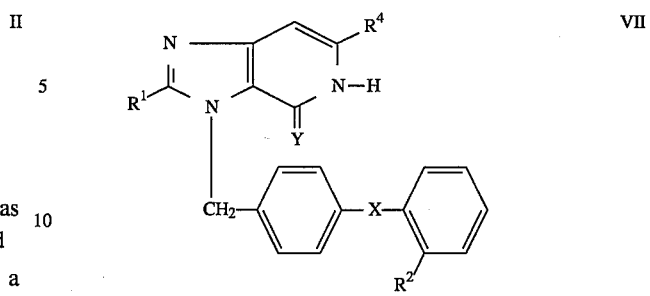 VII wherein

R¹, R², R⁴, X and Y are as defined in formula I, is reacted with a compound of formula VIII:

E—R³     VIII wherein

R³ and E are as defined in formula I, or (e) to prepare a compound of the formula I which contains a —C(=NR¹²)-group, a corresponding carbonyl compound is treated with a compound of the formula H₂N—R¹², wherein R¹² is as defined in formula I, or (f) to prepare a compound where R³ is —C$_n$H$_{2n}$—CO—R¹⁹ and R¹⁹ is —NR⁶R⁷ or —NH—CHR¹⁵—COOA, a carboxylic acid which corresponds to the formula I but instead of the radical R³ contains a —C$_n$H$_{2n}$—COOH group (or one of its functional derivatives) is reacted with a compound of the formula H—R¹⁹ or (g) a compound of formula I is freed from one of its functional derivatives by treatment with a solvolyzing or hydrogenolyzing agent, and/or in that one or more radicals R and/or R² in a compound o f formula I are converted to one or more different radicals R and/or R², and/or a base or acid of formula I is converted to one of its salts.

Above and below, unless expressly indicated otherwise, the radicals or parameters R, R¹ to R¹⁸, X, Y, A, Ar, Het¹, Het², Hal, k, m, n, E, X¹ and X² are as defined in formulae I to VIII.

In the above formulae, A has 1–6, preferably 1, 2, 3 or 4 C atoms. A is preferably methyl, or else ethyl, propyl, isopropyl, butyl, isobutyl, sec-butyl or tertbutyl, or else pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl. Alkenyl is preferably vinyl, prop-1-enyl, prop-2-enyl or but-1-enyl, or else pent-1-enyl or hex-1-enyl. Alkynyl is preferably ethynyl, prop-1-ynyl or prop-2-ynyl, or else but-1-ynyl, pent-1-ynyl or hex-1-ynyl. If several radicals A, alkenyl or alkynyl are present in a compound of the formula I, they can be identical to or different from one another.

Hal is preferably F, Cl or Br, or else I.

R is a radical derived from 3H-imidazo[4,5-c]-pyridine ("3H-IP") or, more precisely, 2-R¹-4-(thi)oxo-5 -R³-6-R⁴-4, 5-dihydro-3H-imidazo[4,5-c]pyridin-3-yl.

Ar is preferably unsubstituted or further, as indicated, monosubstituted phenyl; in detail preferably phenyl, o-, m- or p-tolyl, o-, m- or p-ethylphenyl, o-, m- or p-trifluoromethylphenyl, o-, m- or p-methoxyphenyl, o-, m- or p-ethoxyphenyl, o, m- or p-difluoro-methoxyphenyl, o-, m- or p-trifluoromethoxyphenyl, o-, m- or p-carboxyphenyl, o-, m- or p-methoxycarbonylphenyl, o-, m- or p-ethoxycarbonylphenyl, o-, m- or p-cyanophenyl, o-, m- or p-nitrophenyl, o-, m- or p-aminophenyl, o-, m- or p-acetamidophenyl, o-, m- or p-trifluoroacetamidophenyl, o-, m- or p-methylsulfonamidophenyl, o-, m- or p-trifluoromethylsulfonamidophenyl, o-, m- or p-fluorophenyl, o-, m- or p-chlorophenyl, o-, m- or p-bromophenyl, o-, m- or p-(1H-tetrazol-5-yl)phenyl, furthermore preferably 2,3-, 2,4-, 2,5-, 2,6-, 3,4- or 3,5-dimethylphenyl, 2,3-2,4-, 2,5-2,6-, 3,4- or 3,5-dimethoxyphenyl.

Het$^1$ is preferably tetrahydro-2- or -3-furyl, tetrahydro-2- or -3-thienyl, 1-, 2-, 3- or 3-pyrrolidinyl, 2-, 3-, 4- or 5-oxazolidinyl, 2-, 3-, 4- or 5-thiazolidinyl, 1-, 2-, 3-, 4- or 5-imdazolidinyl, 2-, 3- or 4-tetrayhydropyranyl, 2-, 3- or 4-tetrahydrothiopyranyl, 1-, 2-, 3- or 4-piperidinyl, 2-, 3- or 4-morpholinyl, 1-, 2- or 3-piperazinyl, 1-methyl-2- or -3-pyrrolidinyl, 1-methyl-2-, -3- or -4-piperidinyl, 4-methyl-2- or -3-morpholinyl, 1-methyl-2-, -3- or -4-piperazinyl, 1-phenyl-2- or -3-pyrrolidinyl, 1-phenyl-2-, -3- or -4-piperidinyl, 4-phenyl-2- or -3-morpholinyl, 1-phenyl-2-, -3- or 4-piperazinyl, 2-oxo-3-, -4- or -5-oxazolidinyl, 2-oxo-3-, -4- or -5-thiazolidinyl, 2-oxo-1-, -3-, -4- or -5-imidazolidinyl, 2,4-dioxo-1-, -3- or -5-imidazolidinyl, 2-oxo-3-phenyl-4- or -5-oxazolidinyl, 2-oxo-3 -o-, -m- or -p-tolyl-4- or -5-oxazolidinyl, 2-hydroxyimino-3-, -4- or -5-oxazolidinyl, 2-methoxyimino-3-, -4- or -5-oxazolidinyl, 2-hydroxyimino-4-oxo-3- or -5-oxazolidinyl, 2-methoxyimino-4-oxo-3- or -5-oxazolidinyl.

Het$^2$ is preferably furan-2- or -3-yl, thien-2- or -3-yl, pyrrol-1-, -2- or -3-yl, imidazol-1-, -2-, -4- or -5-yl, pyrazol-1-, -3-, -4- or -5-yl, oxazol-2-, -4- or -5-yl, isoxazol-3-, -4- or -5-yl, thiazol-2-, -4- or -5-yl, isothiazol-3-, -4- or -5-yl, pyridin-2-, -3- or -4-yl or pyrimidin-2-, -4-, -5- or -6-yl, or else preferably 1,2,3-triazol-1-, -4- or -5-yl, 1,2,4 -triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -4-yl, 2,1,5-thiadiazol-3- or -4-yl, pyridazin-3- or -4-yl, pyrazinyl, benzofuran-2-, -3-, -4-, -5-, -6- or -7-yl, benzothien-2-, -3-, -4-, -5-, -6- or -7-yl, indol-1-, -2-, -3-, -4-, -5-, -6- or -7-yl, isoindol-1-, -2-, -3-, -4-, -5-, -6- or -7-yl, benzimidazol-1-, -2-, -4- or -5-yl, benzopyrazol-1-, -3-, -4-, -5-, -6- or -7-yl, benzoxazol-2-, -4, -5-, -6- or -7-yl, benzisoxazol-3-, -4-, -5-, -6- or -7-yl, benzothiazol-2-, -4-, -5-, -6- or -7-yl, benzisothiazol-2-, -4-, -5-, -6- or -7-yl, benz-2,1,3 -oxadiazol-4-, -5-, -6- or -7-yl, quinol-2-, -3-, -4-, -5-, -6-, -7- or -8-yl, isoquinol-1-, -3-, -4-, -5-, -6-, -7- or -8-yl, cinnolin-3-, -4-, -5-, -6-, -7- or -8-yl, quinazol-2-, -4-, -5-, -6-, -7- or -8-yl, 1H-imidazo[4,5-b]pyridin-1-, -2-, -5-, -6- or -7-yl, 3H-imidazo[4,5-b]pyridin-2-, -3-, -5-, -6- or -7-yl, 1H-imidazo[4,5-c]pyridin-1-, -2-, -4-, -6- or -7-yl or 3H-imidazo[4,5-c]pyridin-2-, -3-, -4-, -6- or -7-yl.

The term "Het$^2$" also includes the homologous radicals in which the heteroaromatic ring is substituted by one or more, preferably 1 or 2 groups A, preferably methyl and/or ethyl groups, for example 3-, 4- or 5 -methylfuran-2-yl, 2-, 4- or 5-methylfuran-3-yl, 2,4 -dimethylfuran-3-yl, 3-, 4- or 5-methylthien-2-yl, 3 -methyl-5-tert-butylthien-2-, 2-, 4- or 5-methylthien-3-yl, 2- or 3-methylpyrrol-1-yl, 1-, 3-, 4- or 5-methylpyrrol-2-yl, 3,5-dimethyl-4-ethylpyrrol-2-yl, 2-, 4- or 5-methylimidazol-1-yl, 4-methylpyrazol-5-yl, 4- or 5-methylisoxazol-3-yl, 3- or 5-methylisoxazol-4-yl, 3- or 4-methylisoxazol-5-yl, 3,4-dimethylisoxazol-5-yl, 4- or 5-methylthiazol-2-yl, 4- or 5-ethylthiazol-2-yl, 2- or 5-methylthiazol-4-yl, 2- or 4-methylthiazol-5-yl, 2,4 -dimethylthiazol-5-yl, 3-, 4-, 5- or 6-methylpyridin-2-yl, 2-, 4-, 5- or 6-methylpyridin-3-yl, 2- or 3-methylpyridin-4-yl, 4-methylpyrimidin-2-yl, 4,5-dimethylpyrimidin-2-yl, 2-, 5- or 6-methylpyrimidin-4-yl, 2,6 -dimethylpyrimidin-4-yl, 3-, 4-, 5-, 6- or 7-methylbenzofuran-2-yl, 2-ethylbenzofuran-3-yl, 3-, 4-, 5-, 6- or 7-methylbenzothien-2-yl, 3-ethylbenzothien-2-yl, 1-, 2-, 4-, 5-, 6- or 7 -methylindol-3-yl, 1-methylbenzimidazol-5- or -6-yl or 1-ethylbenzimidazol-5- or -6 -yl.

The groups —C$_k$H$_{2k}$— and —C$_n$H$_{2n}$— are preferably straight-chain and are thus preferably —(CH$_2$)$_n$— and —(CH$_2$)$_k$—, in particular —CH$_2$—, also —CH$_2$CH$_2$—, —(CH$_2$)$_3$—, or —(CH$_2$)$_4$—, but also, for example, —CH(CH$_3$)—, —CH$_2$—CH(CH$_3$)— or —C(CH$_3$)$_2$—. Furthermore, —(CH$_2$)$_n$— can also preferably be —(CH$_2$)$_5$— or —(CH$_2$)$_6$—. The parameter k can preferably also be 0, so that the group —C$_k$H$_{2k}$— is absent.

The radical R$^1$ is preferably straight-chain and is preferably A, in particular ethyl, propyl or butyl, also methyl, pentyl or hexyl, and also cycloalkyl having 3–7 C atoms, in particular cyclopropyl, also cyclobutyl, cyclopentyl, cyclohexyl, cycloheptyl, furthermore in particular alkenyl preferably having 3–6 C atoms, in particular allyl or 1-propenyl, also 1-butenyl, 1-pentenyl or 1-hexenyl; alkynyl preferably having 3–6 C atoms, in particular propargyl or 1-propynyl, also 1-butynyl, 1-pentynyl or 1-hexynyl; cycloalkylalkyl preferably having 4–8 C atoms, in particular cyclopropylmethyl, 1- or 2-cyclopropylethyl, also cyclobutylmethyl, cyclopentylmethyl, cyclohexylmethyl; alkoxy preferably having 1–4 C atoms, such as methoxy, ethoxy, propoxy, butoxy, isobutoxy; alkoxyalkyl preferably having 2–5 C atoms, such as methoxymethyl, ethoxymethyl, propoxymethyl, 2-methoxyethyl, 3-methoxypropyl, 2-ethoxyethyl; alkylthio preferably having 1–4 C atoms such as methylthio, ethylthio, propylthio, butylthio, isobutylthio; alkylthioalkyl preferably having 2–5 C atoms such as methylthiomethyl, ethylthiomethyl, propylthiomethyl, 2-methylthioethyl, 3-methylthiopropyl and 2-ethylthioethyl.

The radical R$^2$ is preferably 1H-tetrazol-5-yl, or else preferably COOH, COOCH$_3$, COOC$_2$H$_5$, CN or NHSO$_2$CF$_3$.

The radical R$^3$ is preferably —C$_n$H$_{2n}$R$^9$ (in detail preferably —CH$_2$R$^9$), in particular —C$_n$H$_{2n}$—CO—NR$^6$R$^7$ (in detail —CH$_2$—CO—NR$^6$R$^7$). Further preferred meanings of the radical R$^3$ are Ar-alkenyl (with 2–6 C atoms in the "alkenyl" moiety, e.g. cinnamyl; —C$_n$H$_{2n}$—C (=NR$^{12}$)—A [in detail —CH$_2$—C(=NR$^{12}$)—A], in particular —C$_n$H$_{2n}$—C(=NOA)—A [in detail —CH$_2$—C(=NOA)—A], e.g. 2-methoxyimino-3,3-dimethylbutyl; Ar-alkenyl substituted in the "alkenyl" moiety by COOA (with 2–6 C atoms in the "alkenyl" moiety), e.g. 3 -ethoxycarbonyl-2 -phenyl-2 -propen-1-yl; —CH (COOA)—Ar, e.g. α-methoxycarbonylbenzyl, α-ethoxycarbonylbenzyl; —C$_n$H$_{2n}$—Het$^1$ (in detail —CH$_2$—Het$^1$), in particular —C$_n$H$_{2n}$—(2-oxo-3 -Ar-5-oxazolidinyl) [in detail —CH$_2$—(2-oxo-3-Ar-5-oxazolidinyl)], e.g. 2-oxo-3-m-tolyl-5-oxazolidinylmethyl. Some more specific preferred radicals R$^3$ are —(CH$_2$)$_t$—CO—NR'R", wherein t is 1 or 2 and R' and R" are H or A, e.g. carbamoylmethyl, 2-carbamoylethyl, N-methylcarbamoylmethyl, 2-N-methylcarbamoylmethyl, N-ethyl-carbamoylmethyl, N-propyl-carbamoylmethyl, N-isopropyl-carbamoylmethyl, N-butyl-carbamoylmethyl, N-isobutylcarbamoylmethyl, N-sec.-butyl-carbamoylmethyl, N-tert.-butylcarbamoylmethyl, N,N-dimethyl-carbamoylmethyl, 2 -N,N-dimethyl-carbamoylethyl, N-methyl-N-ethyl-carbamoylmethyl, N,N-diethyl-carbamoylmethyl, N,N-dipropyl-carbamoylmethyl, N,N-diisopropyl-carbamoylmethyl, N,N-dibutyl-carbamoylmethyl; —(CH$_2$)$_t$—CO—NHAr, for example, N-phenyl-carbamoylmethyl, 2-N-phenyl-carbamoylethyl, N-o-, -m- or -p-tolyl-carbamoylmethyl, N-o-, m- or -p-trifluoromethylphenyl-carbamoylmethyl, N-o-, -m- or -p- carboxyphenyl-carbamoylmethyl, N-o-, -m- or -p-ethoxycarbonyl-phenyl-carbamoylmethyl, N-o-, -m- or p-fluorophenyl-carbamoylmethyl, N-o-, -m- or -p-chlorophenylcarbamoylmethyl, N-(2,3-, N-(2,4-, N-(2,5-, N-(2,6-, N-(3,4- or N-(3,5-dimethylphenyl)-carbamoylmethyl, 2-N-(2,3-, 2-N-(2,4-, 2-N-(2,5-, 2-N-(2,6-, 2-N-(3,4- or 2-N-(3,5-dimethylphenyl)-carbamoylethyl; —(CH$_2$)$_t$—CO—NH—Het$^2$, for example N-(2-, N-(3,- or N-(4-pyridyl)-carbamoylmethyl, 2-N-(2-pyridyl)-carbamoylethyl, N-(2- or N-(3-thienyl)-carbamoylmethyl; —(CH$_2$)$_t$—CO—NAAr, for example, N-methyl-N-phenyl-carbamoylmethyl, 2-N-methyl-N-phenyl-carbamoylethyl, N-ethyl-N-phenyl-carbamoylmethyl; —(CH$_2$)$_t$—CO—NA(C$_n$H$_{2n}$—Ar), for example, N-methyl-N-benzyl-carbamoylmethyl, N-methyl-N-(2-phenylethyl)-carbamoylmethyl, N-methyl-N-(1,1-dimethyl-2-phenylethyl)-carbamoylmethyl, 2-N-methyl-N-(1,1-dimethyl-2-phenylethyl)-carbamoylethyl; —(CH$_2$)$_t$—CO—CH$_2$—NO$_2$, for example 3-nitro-2-oxopropyl, 4-nitro-3-oxopropyl; —(CH$_2$)$_t$—CO—C$_n$H$_{2n}$—NH—COOA, for example 4-BOC-amino-2-oxobutyl, 5-BOC-amino-2-oxopentyl, 6-BOC-amino-2-oxohexyl; —(CH$_2$)—CO—C$_n$H$_{2n}$—NH$_2$, for example 3-amino-2-oxopropyl, 4-amino-2-oxobutyl, 5-amino-2-oxopentyl, 6-amino-2-oxohexyl, 4-amino-3-oxobutyl; —(CH$_2$)$_t$—CO—NH—SO$_2$Ar, for example N-phenylsulfonylcarbamoylmethyl; —(CH$_2$)$_t$—S—A, for example methylthiomethyl; —(CH$_2$)$_t$—SO—A, for example methylsulfinylmethyl; —(CH$_2$)$_t$—SO$_2$—A, for example methyl sulfonylmethyl; —(CH$_2$)$_t$—S—Ar, for example phenylthiomethyl; —(CH$_2$)$_t$—SO—Ar, for example phenylsulfinylmethyl; —(CH$_2$)$_t$—SO$_2$—Ar, for example phenylsulfonylmethyl, —(CH$_2$)$_t$—S—Het$^2$, for example (2-thienyl)thiomethyl; —(CH$_2$)$_t$—SO—Het$^2$, for example (2-pyridyl)sulfinylmethyl; —(CH$_2$)$_t$—SO$_2$—Het$^2$, for example (2-, (3- or (4-pyridyl)-sulfonylmethyl.

The radical R$^4$ is preferably H, or else F, Cl, Br or I.

Preferably, the radicals R$^5$ and R$^8$ contain 1, 2 or 3 C atoms and are preferably methyl, ethyl, trifluoromethyl, pentafluoroethyl, 2,2,2-trifluoroethyl or 3,3,3-trifluoropropyl. If a compound of formula I contains two radicals R$^5$, these can be identical to or different from one another.

The radicals R$^6$ and R$^7$ are preferably H or A, R$^6$ is additionally preferably Ar, Ar—C$_n$H$_{2n}$ or Het$^2$.

Further preferred groups —NR$^6$R$^7$ are those in which R$^6$ and R$^7$ together are an alkylene chain having 2–5 C atoms, which can be substituted as indicated and/or interrupted by O or by —NR$^{16}$—. Particularly preferred groups —NR$^6$R$^7$ of this type are, for example, aziridino, pyrrolidino, piperidino, morpholino, piperazino, 2-oxopyrrolidino, 2-alkoxycarbonylpyrrolidino (wherein the alkoxy group contains 1–4 C atoms), such as 2-methoxycarbonylpyrrolidino or 2-ethoxycarbonylpyrrolidino, 2- or 3-alkanoylaminopyrrolidino such as 2- or 3-acetamidopyrrolidino, 2-, 3- or in particular 4-oxopiperidino, 2-, 3- or in particular 4-Arpiperidino such as 2-, 3- or 4-phenylpiperidino, 4-o-, 4-m- or 4-p-methoxyphenylpiperidino, 4-o-, 4-m- or 4-p-nitrophenylpiperidino, 4-o-, 4-m- pr 4-p-chlorophenylpiperidino, 3-hydroxymethyl-4-p-chlorophenylpiperidino, 2-, 3- or 4-(2-thienyl)piperidino, 2-, 3- or 4-N,N-dimethylcarbamoylpiperidino, 2-, 3- or 4-N,N-diethylcarbamoylpiperidino, 2-, 3- or 4-benzoylpiperidino, 2-, 3- or 4-p-methoxybenzoylpiperidino, 4-methylpiperazino, 4-phenylpiperazino, 4-o-, 4-m- or 4-p-methoxyphenylpiperazino, 4-o-, 4-m- or 4-p-nitrophenylpiperazino, 4-o-, 4-m- or 4-p-chlorophenylpiperazino, 4-(2-pyrimidinyl)piperazino, 4-methoxycarbonylpiperazino, 4-ethoxycarbonylpiperazino, 4-BOC-piperazino, 4-phenylsulfonylpiperazino, 4-p-tolylsulfonylpiperazino, 4-o-, 4-m- or 4-p-fluorophenylsulfonylpiperazino.

R$^9$ is preferably —CO—NR$^6$R$^7$, further preferably —CO—R$^{14}$ or —C(=NR$^{12}$)—A.

R$^{10}$ is preferably COOH or COOA.

R$^{11}$ is preferably Ar, in particular phenyl,

R$^{12}$ is preferably OH or OR$^{13}$, in particular OA:

R$^{13}$ is preferably A.

R$^{14}$ is preferably —C$_n$H$_{2n}$—NO$_2$ or —C$_n$H$_{2n}$—NR$^6$R$^7$, in particular —C$_n$H$_{2n}$NH$_2$.

R$^{15}$ is preferably H, further A having 1–4 C atoms.

m is preferably 0 or 2.

n is preferably 1, further preferably 2, 3 or 4.

Preferably, the radical X is absent or is —NH—CO— or —CO—NH—.

The radical Y is preferably O, or else S.

The compounds of formula I can possess one or more chiral centers and can therefore exist in different forms (optically active or optically inactive). Formula I includes all these forms.

Accordingly the invention relates especially to those compounds of formula I in which at least one of said radicals has one of the preferred meanings indicated above. Some preferred groups of compounds can be expressed by the following partial formulae Ia to Ii, which correspond to formula I and wherein the radicals not described more precisely are as defined in formula I, except that:

in Ia: X is absent;

in Ib: X is —NH—CO—;

in Ic: X is —CO—NH—;

in Id: X is —O—CH(COOH)—;

in Ie: X is —NH—CH(COOH)—;

in If: X is —CH=C(COOH)—;

in Ig: X is —CH=C(CN)—;

in Ih: X is —CH=C(1H-tetrazol-5-yl)—.

Compounds of formula Ia are particularly preferred.

The following are also preferred:

compounds of formulae Ik and Iak to Ihk, which correspond to the compounds of formulae I and Ia to Ih, except that in addition Y is an O atom;

compounds of formulae Il, Ial to Ikl and Iakl to Ihkl, which correspond to formulae I, Ia to Ik and Iak to Ihk, except that in addition R$^4$ is H;

compounds of formulae Im, Iam to Ilm, Ialm to Iklm and Iaklm to Ihklm, which correspond to formulae I, Ia to Il, Ial to Ikl and Iakl to Ihkl, except that in addition R$^2$ is CN or 1H-tetrazol-5-yl.

Among these, preferred compounds are those in which R$^1$ is A or alkenyl each having 3–6 C atoms.

Other preferred groups of compounds have formula I and the other formulae given above, except that the radical R$^3$ is defined as follows:

(a) alkenyl—Ar with 2–6 C atoms in the "alkenyl" moiety (b) —C$_n$H$_{2n}$—R$^9$, (c) —CHR$^{10}$—AR, (d) —C$_n$H$_{2n}$—CO—NR$^6$R$^7$, (e) —(CH$_2$)$_t$—CO—NR'R" (wherein t is 1 or 2, R' and R" are each H or A), (f) —CH$_2$—CO—NR$^6$R$^7$, wherein R$^6$ and R$^7$ together are an alkylene chain having 2–5 C atoms, which can be monosubstituted or polysubstituted by carbonyl oxygen, Ar, Het$^2$, —CO—Ar, —COOA, —CO—N(A)$_2$, —CH$_2$OH, —SO$_2$—Ar and/or —NH—

CO—A and/or interrupted by O or by —NR$^{16}$—,
(g) —CH$_2$—CO—NR$^6$R$^7$, wherein —NR$^6$R$^7$ is pyrrolidino, piperidino, morpholino, 3-acetamidopyrrolidino, 4-oxopiperidino, 3-diethylaminocarbonylpiperidino, 4-o-methoxyphenylpiperidino, 4-o-methoxyphenylpiperazino, 4-o-nitrophenylpiperazino or 4-p-fluorophenylsulfonylpiperazino.

A small selected group of preferred compounds has formula I wherein

R is a 2-butyl-4,5-dihydro-4-oxo-5-R$^3$-3H-imidazo[4,5-c]-pyridin-3-yl radical, R$^2$ is 1H-tetrazol-5-yl, R$^3$ is —C$_n$H$_{2n}$—CONR$^6$R$^7$ and X is absent.

The compounds of formula I and also the starting materials for their preparation are moreover prepared by methods known per se, such as those described in the literature (for example in the standard works like Houben-Weyl, Methoden der organischen Chemie (Methods of Organic Chemistry), Georg-Thieme-Verlag, Stuttgart, but especially in European patent application A2-0 430 709 and U.S. Pat. No. 4,880,804), under conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of formula I.

The compounds of formula I can preferably be obtained by reacting compounds of formula II with compounds of formula III. Particularly the biphenyl derivatives of formula I (wherein X is absent) are readily obtainable in this way.

In the compounds of formula II, E is preferably Cl, Br, I or an OH group which has been functionally modified to acquire reactivity, such as alkylsulfonyloxy having 1–6 C atoms (preferably methylsulfonyloxy) or arylsulfonyloxy having 6–10 C atoms (preferably phenyl- or p-tolyl-sulfonyloxy).

The reaction of II with III is conveniently carried out by first converting III to a salt by treatment with a base, for example with an alkali metal alcoholate such as CH$_3$ONa or potassium tert-butylate in an alcohol such as methanol or tert-butanol, or with an alkali metal hydride such as NaH, or with an alkali metal alcoholate in dimethylformamide (DMF), and then reacting said salt with II in an inert solvent, for example an amide such as DMF, N-methylpyrrolidone or dimethylacetamide, or a sulfoxide such as dimethyl sulfoxide (DMSO), conveniently at temperatures of preferably about –20°–100°, particularly 10°–30°. Other suitable bases are alkali metal hydrogen carbonates such as NaHCO$_3$ or KHCO$_3$.

The compounds of formula I can also be obtained by the cyclization of compounds of formula IV. This cyclization is conveniently carried out by heating with polyphosphoric acid, acetic acid or diglyme to temperatures of preferably about 80°–180°, particularly 120°–160°.

Acid amides of formula I (X=—NH—CO— or —CO—NH—) can also be obtained by reacting compounds of formula V (or reactive derivatives thereof) with compounds of formula VI (or reactive derivatives thereof).

Suitable reactive derivatives of the carboxylic acids of formulae V and VI (X$^1$ or X$^2$=COOH) are advantageously the corresponding chlorides, bromides or anhydrides. The reaction is conveniently carried out in the presence of an inert solvent, for example a halogenated hydrocarbon such as methylene chloride, chloroform, trichloroethene or 1,2-dichloroethane, or an ether such as tetrahydrofuran (THF) or dioxane, at temperatures of preferably about 0°–150°, especially 20°–80°. If acid halides are reacted, it is recommended to add a base, for example a tertiary amine such as triethylamine, pyridine or 4-dimethylaminopyridine.

The compounds of formula I can also be obtained by reacting a compound of formula VII (corresponding to formula I but with H in place of R$^3$) with a compound of formula VIII. This reaction is preferably carried out in an inert solvent, for example an acid amide such as DMF, N-methylpyrrolidone, 1,3- dimethyl-2-oxohexahydropyrimidine or hexamethylphosphorotriamide, an alcohol such as methanol or tert-butanol, an ether such as THF, or a halogenated hydrocarbon such as methylene chloride, or mixtures thereof, as the solvent, and/or in the presence of an alkali metal alcoholate such as sodium methylate or potassium tert-butylate, an alkali metal hydride such as sodium or potassium hydride, an alkali metal carbonate such as sodium or potassium carbonate, an alkali metal bicarbonate such as sodium or potassium bicarbonate, or a tertiary amine such as triethylamine or ethyldiisopropylamine, at temperatures of preferably about –30–200, particularly 20°–60°.

Compounds of the formula I which contain the group —C(=NR$^{12}$)— can be prepared from carbonyl compounds which, instead, contain the group —CO— but otherwise correspond to the formula I, by reaction with a compound of the formula H$_2$N—R$^{12}$. These last-mentioned compounds include ammonia, hydroxylamine, O-alkyl-, O-alkenyl-, O-alkynyl- and O-arylhydroxylamines, cyanamides and primary amines of the formula R$^{13}$—NH$_2$.

Compounds of the formula I in which R$^3$ is —C$_n$H$_{2n}$—CO—R$^{19}$ can also be obtained by reaction of carboxylic acids which correspond to the formula I, but instead of the radical R$^3$ contain a —C$_n$H$_{2n}$—COOH group, with amines of the formula H-R$^{19}$. In this case, the reaction is expediently carried out by customary methods of peptide synthesis, such as are described, for example, in Houben-Weyl, l.c., Volume 15/II, pages 1–806 (1974).

The reaction preferably takes place in the presence of a dehydrating agent, for example of a carbodiimide such as N,N'-dicyclohexylcarbodiimide ("DCCI"), 1,1'-carbonyldiimidazole or N-3-dimethylaminopropyl-N'-ethylcarbodiimide ("DAPECI"), also propanephosphonic anhydride (cf. Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, an ether such as THF or dioxane, an amide such as DMF or dimethylacetamide, a nitrile such as acetonitrile, at temperatures of preferably about –10–40, particularly 0°–30°.

Instead of the carboxylic acids, suitable reactive derivatives of these substances can also be employed in the reaction, for example those in which reactive groups are intermediately blocked by protective groups. The acids can be used, for example, in the form of their activated esters which are expediently formed in situ, for example by addition of 1-hydroxybenzotriazole or N-hydroxysuccinimide.

It is also possible to free a compound of formula I from one of its functional derivatives by solvolysis (for example hydrolysis) or hydrogenolysis.

Thus carboxylic acids of formula I wherein X is —O—CH(COOH), —NH—CH(COOH), —NA—CH(COOH) or —CH=C(COOH) can be obtained by the saponification of corresponding alkyl esters, for example with NaOH or KOH in aqueous solution, with or without the addition of an inert organic solvent such as methanol, ethanol, THF or dioxane, at temperatures of preferably about 0°–100°, or by the hydrogenolysis of corresponding benzyl esters, for example on Pd-on-charcoal at pressures of preferably about 1–200 bar and at temperatures of preferably about 0°–100°, in one of the inert solvents indicated.

It is also possible, using one of the methods indicated, to prepare a compound which has formula I but in which a tetrazol-5-yl group is replaced with a 1H(or 2H)—tetrazol-5-yl group functionally modified in the 1-position (or 2-position) (protected by a protecting group). Examples of suitable protecting groups are: triphenylmethyl, which can be cleaved with HCl or formic acid in an inert solvent or solvent mixture, for example ether/methylene chloride/methanol; 2-cyanoethyl, which can be cleaved with NaOH in water/THF; and p-nitrobenzyl, which can be cleaved with $H_2$/Raney nickel in ethanol (compare European patent application A2-0 291 969).

Some of the starting materials, especially those of formulae II, VI and VIII, are known. If they are not known, they can be prepared by known methods analogously to known substances. Compounds of formula III (Y=O) can be obtained, for example, by reacting carboxylic acids of the formula $R^1$—COOH with compounds of formula IX:

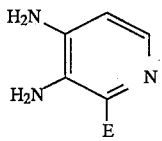

IX in the presence of polyphosphoric acid; the group E (preferably Cl) is hydrolyzed in the process and compounds of formula III in which $R^3$=H are formed initially; these are then reacted with compounds of formula VIII.

Compounds of formula IV can be obtained for example by reacting compounds of formula X:

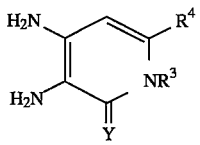

X wherein, however, one of the amino groups is protected by an amino-protecting group (for example benzyl, A— — CO— or benzyloxycarbonyl), with compounds of formula II and subsequently cleaving the protecting group and reacting the products with acids of the formula $R^1$—COOH or functional derivatives thereof; they are not normally isolated, but are formed in situ in the last-mentioned reaction.

Compounds of formula V can be prepared by reacting III with benzyl chlorides of the formula Cl— $CH_2$—p— $C_6H_4$—$X^3$ (wherein $X^3$ is a protected $NH_2$ or COOH group) and subsequently cleaving the protecting group.

Compounds of formula VII can be obtained for example by reacting compounds of formula III, carrying an H atom in place of $R^3$, with compounds of formula II.

It is also possible to convert one compound of formula I to another compound of formula I by converting one or more of the radicals R and/or $R^2$ to other radicals R and/or $R^2$, for example by reducing nitro groups to amino groups (for example by hydrogenation on Raney nickel or Pd-on-charcoal in an inert solvent such as methanol or ethanol), and/or functionally modifying free amino and/or hydroxyl groups, and/or freeing functionally modified amino and/or hydroxyl groups by solvolysis or hydrogenolysis, and/or hydrolyzing nitrile groups to COOH groups, or converting nitrile groups to tetrazolyl groups with hydrazoic acid derivatives, for example sodium azide in N-methylpyrrolidone or trimethyltin azide in toluene, and/or oxidizing thioether groups to SO or $SO_2$ groups, for example with $H_2O_2$ or a peracid such as 3-chloroperbenzoic acid.

Thus, for example, free amino groups can be acylated in conventional manner with an acid chloride or anhydride, or alkylated with an unsubstituted or substituted alkyl halide, conveniently in an inert solvent such as methylene chloride or THF, and/or in the presence of a base such as triethylamine or pyridine, at temperatures of preferably about −60°–+30°.

If desired, a functionally modified amino and/or hydroxyl group in a compound of formula I can be freed by solvolysis or hydrogenolysis using conventional methods. Thus, for example, a compound of formula I containing an $NHCOR^5$ or COOA group can be converted to the corresponding compound of formula I containing an $NH_2$ or HOOC group instead. COOA groups can be saponified for example with NaOH or KOH in water, water/THF or water/dioxane, at temperatures of preferably about 0°–100°.

The reaction of nitriles of formula I (for example those in which $R^2$=CN) with hydrazoic acid derivatives leads to tetrazoles of formula I (for example in which $R^2$=1H-tetrazol-5-yl). It is preferable to use trialkyltin azides such as trimethyltin azide, in an inert solvent, for example an aromatic hydrocarbon such as toluene, at temperatures of preferably about 20°–150°, particularly 80°–140°, or sodium azide in N-methylpyrrolidone at temperatures of preferably about 100°–200°. The trialkyl tin group is then eliminated, either by treating with hydrochloric acid, for example in dioxane, or with alkali, for example in ethanol/water, or with formic acid, for example in methanol, or by chromatography on a silica gel column, for example using ethyl acetate/methanol.

A base of formula I can be converted with an acid to the corresponding acid addition salt, for example by reaction of equivalent amounts of the base and of the acid in an inert solvent such as ethanol and subsequent evaporation. Possible acids for this reaction are especially those which yield physiologically acceptable salts. Thus it is possible to use inorganic acids, for example sulfuric acid, nitric acid, hydrohalic acids such as hydrochloric acid or hydrobromic acid, phosphorus acids such as orthophosphoric acid, and sulfamic acid, as well as organic acids, especially aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid. Salts with physiologically unacceptable acids, for example picrates, can be used for isolating and/or purifying the compound of formula I.

On the other hand, compounds of formula I containing COOH or tetrazolyl groups can be converted with bases (for example sodium or potassium hydroxide or carbonate) to the corresponding metal salts, especially alkali metal or alkaline earth metal salts, or to the corresponding ammonium salts. The potassium salts of the tetrazolyl derivatives are particularly preferred.

The novel compounds of formula I and their physiologically acceptable salts can be used for the manufacture of pharmaceutical preparations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (for example oral or rectal) or parenteral administration or for administration in the form of an inhalation spray, and which do not react with the novel compounds, examples being water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; special lacquered tablets and capsules with coatings or shells resistant to gastric juices are of interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant gas mixture. It is convenient here to use the active ingredient in micronized form, it being possible for one or more additional physiologically compatible solvents, for example ethanol, to be present. Inhalation solutions can be administered with the aid of conventional inhalers. The novel compounds can be lyophilized and the resulting lyophilizates used for example for the manufacture of injectable preparations. The indicated formulations can be sterilized and/or can contain adjuncts such as preservatives, stabilizers and/or wetting agents, emulsifiers, salts for influencing the osmotic pressure, buffer substances and colors and/or flavorings. If desired, they can also contain one or more other active ingredients, for example one or more vitamins, diuretics or antiphlogistics.

The substances according to the invention are normally administered analogously to other known, commercially available preparations (e.g., Enalapril and Captopril), but in particular analogously to the compounds described in U.S. Pat. No. 4,880,804, preferably in doses of about 1 mg–1 g, especially 50–500 mg per dosage unit. The daily dose is preferably about 0.1–50 mg/kg, especially 1–10 mg/kg of body weight. However, the particular dose for each individual patient depends on a very wide variety of factors, for example on the efficacy of the particular compound used, age, body weight, general state of health, sex, diet, time and mode of administration, rate of excretion, drug combination and severity of the particular disease to which the therapy is applied. Oral administration is preferred.

Above and below, all temperatures are given in ° C. In the following Examples, "conventional working-up" means: Water is added if necessary, the pH is adjusted to preferably about 2–10 if necessary, depending on the constitution of the end product, extraction is carried out with ethyl acetate or methylene chloride and the organic phase is separated off, dried over sodium sulfate, evaporated and purified by chromatography on silica gel and/or by crystallization.

IP=imidazo[4,5-c]pyridine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosure of all applications, patents and publications, cited above and below, and of corresponding German applications P 42 19 818.6 and P 43 05 602.4, are hereby incorporated by reference.

EXAMPLES

EXAMPLE 1

(a) A solution of 0.23 g of Na in 20 ml of methanol is added dropwise over 15 minutes to a solution of 2.76 g of 2-butyl-5-N,N-dimethylcarbamoylmethyl-4,5-dihydro-4-oxo-3H-IP [obtainable by condensation of valeric acid with 3,4-diamino-2-chloropyridine, in the presence of polphosphoric acid, to give 2-butyl-4,5-dihydro-4-oxo-1(or 3)H-IP, reaction with benzyl bromide in methanol, in the presence of $CH_3ONa$, to give 3-benzyl-2-butyl-4,5 -dihydro-4-oxo-3H-IP, reaction with N,N-dimethyl-chloroacetamide in DMF, in the presence of potassium tertbutylate, to give 3-benzyl-2-butyl-5-(N,N-dimethylcarbamoylmethyl)- 4,5-dihydro-4-oxo-3H-IP, and hydrogenolytic cleavage of the benzyl group] in 75 ml of methanol. The mixture is stirred for a further 30 minutes at 20° and evaporated, the residue is dissolved in 20 ml of DMF, and a solution of 3.05 g of methyl 4'-bromomethylbiphenyl-2-carboxylate (IIa) in 10 ml of DMF is added dropwise at 0°, with stirring. The mixture is stirred for 16 hours at 20°, evaporated, worked up in conventional manner and chromatographed on silica gel to give 2-butyl-5-(N,N-dimethylcarbamoylmethyl)4,5-dihydro- 3-(2'-methoxycarbonylbiphenyl-4-ylmethyl)-4oxo-3H-IP.

(b) A mixture of 1 g of the methyl ester obtained according to (a), 12 ml of 2N aqueous NaOH solution and 48 ml of methanol is boiled for 2 hours and then evaporated. The residue is worked up in conventional manner (aqueous hydrochloric acid to pH 3/methylene chloride) to give 2-butyl-5-(N,N-dimethylcarbamoylmethyl)-4,5-dihydro-3-(2'-carboxybiphenyl-4ylmethyl)4-oxo- 3H-IP.

EXAMPLE 2

2-Butyl-3-[p-(1-cyano-2-phenylvinyl)benzyl]-4,5-dihydro- 4-oxo-5-(N,N-dimethylcarbamoylmethyl)-3H-IP is obtained analogously to Example 1 from 2.76 g of 2-butyl-4,5-dihydro-4-oxo-5-(N,N-dimethylcarbamoylmethyl)-3H-IP and 2.98 g of 3-p-bromomethylphenyl-2-phenylacrylonitrile [m.p. 178°: obtainable by condensation of p-tolylaldehyde with phenylacetonitrile in ethanol, in the presence of $C_2H_5ONa$, to give 2-phenyl-3-p-tolylacrylonitrile (m.p. 61°), and bromination with N-bromosuccinimide in methylene chloride].

EXAMPLE 3

A mixture of 1.02 g of valeric acid, 4.44 g of 4-amino-1,2-dihydro-2-oxo-3-2'-(1H-tetrazol-5-yl)biphenyl-4-ylmethylamino]-1-(N,N-dimethylcarbamoylmethyl)pyridine [obtainable by reaction of 3-amino-4-benzylamino-1,2-dihydro-2-oxo-1-(N,N-dimethylcarbamoylmethyl)pyridine with 4-bromomethyl-2'-cyanobiphenyl to give 4-benzylamino-3-(2'-cyanobiphenyl-4-ylmethylamino)-1,2-dihydro-2-oxo-3-[2'-(1H-tetrazol-5-yl)biphenyl- 4-ylmethylamino]-1-(N,N-dimethylcarbamoylmethyl)pyridine, and hydrogenolytic cleavage of the benzyl group] and 50 g of polyphosphoric acid is heated for 5 hours at 140°. 4-Amino-1,2-dihydro-2-oxo-3-[N-(2'-(1H-tetrazol-5-yl)-biphenyl-4-ylmethyl-N-valerylamino]-1-(N,N-dimeylcarbamoylmethyl)pyridine and 1,2-dihydro-2-oxo-3-[2'-(1H-tetrazol-5 -yl)biphenyl-4-ylmethylamino]-1-(N,N-dimethylcarbamoylmethyl)-4-valerylaminopyridine are formed in situ as intermediates. The mixture is cooled, poured onto ice, rendered alkaline with sodium hydroxide solution and worked up in conventional manner to give 2-butyl-4,5-dihydro-5-(N,N-dimethylcarbamoylmethyl)-4-oxo-3-2'-(1H-tetrazol-5-yl)biphenyl-4 -ylmethyl]-3H-IP, m.p. 258°.

EXAMPLE 4

A mixture of 1.1 g of 3-p-aminobenzyl-2-butyl-4,5-dihydro-5-(N,N-dimethylcarbamoylmethyl)-4-oxo-3H-IP [obtainable by reaction of 2-butyl-4,5-dihydro-5-(N,N-dimethylcarbamoylmethyl)-4-oxo-3H-IP with p-nitrobenzyl bromide to give 2-butyl-4,5-dihydro-5-(N,N-dimethylcarbamoylmethyl)-3-p-nitrobenzyl-4-oxo-3H-IP, and subsequent hydrogenation], 0.6 g of phthalic anhydride and 40 ml of CHCl$_3$ is stirred for 16 hours at 20°. The 2-butyl-3-[4-(o-carboxybenzamido)benzyl]-4,5-dihydro-5 -(N,N-dimethylcarbamoylmethyl)-4-oxo-3H-IP which has precipitated out is filtered off.

EXAMPLE 5

A mixture of 3.81 g of 3-p-aminobenzyl-2-butyl-4,5-dihydro-5-(N,N-dimethylcarbamoylmethyl)-4-oxo-3H-IP, 3 ml of triethylamine, 0.5 g of 4-dimethylaminopyridine and 120 ml of methylene chloride is cooled to 5° and a solution of 2.88 g of o-trifluoromethanesulfonamidobenzoyl chloride in 20 ml of methylene chloride is added dropwise. The mixture is stirred for a further 16 hours at 20°, evaporated and worked up in conventional manner to give 2-butyl-4,5-dihydro-5-(N,N-dimethylcarbamoylmethyl)-4-oxo-3-[4-(o-trifluoromethanesulfonamidobenzamido)benzyl]-3H-IP.

EXAMPLE 6

A mixture of 4.10 g of 2-butyl-3-p-carboxybenzyl-4,5-dihydro-5-(N,N-dimethylcarbamoylmethyl)-4-oxo-3H-IP, 12 g of thionyl chloride and 35 ml of CHCl$_3$ is boiled for 6 hours and evaporated. The crude acid chloride obtained is freed of thionyl chloride residues by dissolution in toluene several times, followed each time by evaporation, and is dissolved in 80 ml of THF. This solution is added dropwise to a solution of 1.7 g of anthranilic acid and 0.8 g of NaOH in 100 ml of water and the mixture is stirred for 24 hours and acidified to pH 5 with hydrochloric acid. 2-Butyl-3-[p-(2-carboxyanilinocarbonyl)benzyl]-4,5-dihydro-5-(N,N-dimethylcarbamoylmethyl)-4-oxo-3H-IP is obtained after conventional working-up.

EXAMPLE 7

(a) 1.25 g of potassium tert-butylate are added at 20° to a solution of 3.1 g of 2-butyl-3-(2'-cyanobiphenyl-4-ylmethyl)-4,5-dihydro-4-oxo-3H-IP (m.p. 179°–180°; obtainable from 2-butyl-4,5-dihydro-4-oxo-1(or 3)H-IP with 4'-bromomethyl-2-cyanobiphenyl in DMF, in the presence of K$_2$CO$_3$) in 35 ml of DMF, with stirring. After stirring for 45 minutes, a solution of 2.54 g of N,N-dimethylchloroacetamide in 25 ml of DMF is added dropwise. The mixture is stirred for a further 16 hours at 20° and worked up in conventional manner to give 2-butyl-3-(2'-cyanobiphenyl-4-ylmethyl)-4,5-dihydro-5-(N,N-dimethylcarbamoylmethyl)-4-oxo-3H-IP.

The following 2-butyl-3-(2'-cyanobiphenyl-4-ylmethyl)-4,5-dihydro-4-oxo-5-R$^3$-3H-IP are obtained analogously:
with cinnamyl bromide:
    -5-cinnamyl-[=5-(3-phenyl-2-propen-1-yl)-]
with 3-ethoxycarbonyl-2-phenyl-2-propen-1-yl bromide (=ethyl β-bromomethylcinnamate):
    -5-(3-ethoxycarbonyl-2-phenyl-2-propen-1-yl)-
with methyl α-bromophenyl acetate:
    -5-(α-methoxycarbonyl-benzyl)-
with 2-methoxyimino-3,3-dimethylbutyl bromide:
    -5-(2-methoxyimino-3,3-dimethylbutyl)-
with 2-oxo-3-m-tolyl-5-oxazolidinylmethyl bromide:
    -5-(2-oxo-3-m-tolyl-5-oxazolidinyl-methyl)-
with bromoacetamide:
    -5-carbamoylmethyl-, m.p. 219°
with N-methylchloroacetamide:
    -5-(N-methyl-carbamoylmethyl)-
with N-ethylchloroacetamide:
    -5-(N-ethylcarbamoylmethyl)-
with N-tert-butylchloroacetamide:
    -5-(N-tert-butyl-carbamoylmethyl)-
with N,N-diethylchloroacetamide:
    -5-(N,N-diethylcarbamoylmethyl)-
with N,N-diisopropylchloroacetamide:
    -5-(N,N-diisobutylcarbamoylmethyl)-, m.p. 170°
with N-phenylchloroacetamide:
    -5-(N-phenylcarbamoylmethyl)-, m.p. 107°
with N-o-tolylchloroacetamide:
    -5-(N-o-tolylcarbamoylmethyl)-, m.p. 175°
with N-o-trifluoromethylphenylchloroacetamide:
    -5-(N-o-trifluoromethylphenylcarbamoylmethyl)-
with N-o-ethoxycarbonylphenylchloroacetamide:
    -5-(N-o-ethoxycarbonylphenylcarbamoylmethyl)-
with N-o-chlorophenylchloroacetamide:
    -5-(N-o-chlorophenylcarbamoylmethyl)-
with N-(2,6-dimethylphenyl)chloroacetamide:
    -5-[N-(2,6-dimethylphenyl)carbamoylmethyl]-
with N-(2-pyridyl)chloroacetamide:
    -5-[N-(2-pyridyl)carbamoylmethyl]-
with N-methyl-N-phenylchloroacetamide:
    -5-(N-methyl-N-phenylcarbamoylmethyl)-,m.p. 106°
with N-methyl-N-(1,1-dimethyl-2-phenylethyl)chloroacetamide:
    -5-[N-methyl-N-(1,1-dimethyl-2-phenylethyl)carbamoylmethyl]-
with N,N-diphenylchloroacetamide:
    -5-(N,N-diphenylcarbamoylmethyl)-
with 3-chloropropionamide:
    -5-(2-carbamoylethyl)-
with 3-chloro-N,N-dimethylpropionamide:
    -5-(2-N,N-dimethylcarbamoylethyl)-
with 3-chloro-N-phenylpropionamide:
    -5-(2-N-phenylcarbamoylethyl)-
with 3-chloro-N-(2,6-dimethylphenyl)propionamide:
    -5-[2-N-(2,6-dimethylphenyl)carbamoylethyl]-
with 1-chloro-3-nitroacetone:
    -5-(3-nitro-2-oxopropyl)-
with 6-BOC-amino-1-chloro-2-hexanone:
    -5-(6-BOC-amino-2-oxohexyl).
with chloroacetic acid N-ethoxycarbonylmethyl-N-methylamide:
    -5-(N-ethoxycarbonylmethyl-N-methyl-carbamoylmethyl)
with chloroacetic acid N-(methylsulfonyl)amide:
    -5-(N-methylsulfonylcarbamoylmethyl)-
with chloroacetic acid N-(phenylsulfonyl)amide:

-5-(N-phenylsulfonylcarbamoylmethyl)-, m.p. 193°
with chloroacetic acid aziridide:
  -5-aziridinocarbonylmethyl-
with chloroacetic acid pyrrolidide:
  -5-pyrrolidinocarbonylmethyl-, m.p. 166°
with chloroacetic acid piperidide:
  -5-piperidinocarbonylmethyl-
with chloroacetic acid 2-oxopyrrolidide:
  -5-(2-oxopyrrolidinocarbonylmethyl)-
with chloroacetic acid 2-oxopiperidide:
  -5-(2-oxopiperidinocarbonylmethyl)-
with chloroacetic acid 4-oxopiperidide:
  -5-(4-oxopiperidinocarbonylmethyl)-
with chloroacetic acid 4-o-methoxyphenylpiperidide:
  -5-(4-o-methoxyphenyl-piperidinocarbonylmethyl)-
with chloroacetic acid 4-(2-thienyl)piperidide:
  -5-[4-(2-thienyl)piperidinocarbonylmethyl]-
with chloroacetic acid 4-p-methoxybenzoylpiperidide:
  -5-(4-p-methoxybenzoylpiperidinocarbonylmethyl)-
with chloroacetic acid 2-ethoxycarbonylpyrrolidide:
  -5-(2-ethoxycarbonylpyrrolidinocarbonylmethyl)-
with chloroacetic acid 3-ethoxycarbonylpiperidide:
  -5-(3-ethoxycarbonylpiperidinocarbonylmethyl)-
with chloroacetic acid 3-hydroxymethyl-4-p-chlorophenylpiperidide:
  -5-(3-hydroxymethyl-4-p-chlorophenylpiperidinocarbonylmethyl)-
with chloroacetic acid 3-N,N-diethylcarbamoylpiperidide:
  -5-(3-N,N-diethylcarbamoylpiperidinocarbonylmethyl-, m.p. 97°
with chloroacetic acid 3-acetamidopyrrolidide:
  -5-(3-acetamidopyrrolidinocarbonylmethyl)-
with chloroacetic acid morpholide:
  -5-morpholinocarbonylmethyl-
with chloroacetic acid 3-oxo-piperazide:
  -5-(3-oxopiperazinocarbonylmethyl)-
with chloroacetic acid 4-methylpiperazide:
  -5-(4-methylpiperazinocarbonylmethyl)-
with chloroacetic acid 4-o-methoxyphenylpiperazide:
  -5-(4-o-methoxyphenylpiperazinocarbonylmethyl)-
with chloroacetic acid 4-o-nitrophenylpiperazide:
  -5-(4-nitrophenylpiperazinocarbonylmethyl)-
with chloroacetic acid 3-ethoxycarbonylpiperazide:
  -5-(3-ethoxycarbonylpiperazinocarbonylmethyl)-
with chloroacetic acid 4-BOC-piperazide:
  -5-(4-BOC-piperazinocarbonylmethyl)-
with chloroacetic acid 4-(2-pyrimidinyl)piperazide:
  -5-[4-(2-pyrimidinyl)piperazinocarbonylmethyl]-
with chloroacetic acid 4-p-fluorophenylsulfonylpiperazide:
  -5-(4-p-fluorophenylsulfonylpiperazinocarbonylmethyl)- m.p. 207°
with methylthiomethyl chloride:
  -5-methylthiomethyl-
with methylsulfinylmethyl chloride:
  -5-methylsulfinylmethyl-
with methylsulfonylmethyl chloride:
  -5-methylsulfonylmethyl-
with phenylthiomethyl chloride:
  -5-phenylthiomethyl-, m.p. 105°
with phenylsulfinylmethyl chloride:
  -5-phenylsulfinylmethyl-, m.p. 115°
with phenylsulfonylmethyl bromide:
  -5-phenylsulfonylmethyl-
with 2-thienylthiomethyl chloride:
  -5-(2-thienylthiomethyl)-
with 2-pyridylaminosulfonylmethyl chloride:
  -5-(2-pyridylaminosulfonylmethyl)-
with methoxysulfonylmethyl chloride:
  -5-methoxysulfonylmethyl-.

(b) A mixture of 3.95 g of the compound obtained according to (a), 20.6 g of trimethyltin azide and 200 ml of toluene is boiled for 24 hours and then evaporated. The residue is taken up in 100 ml of methanolic HCl and the mixture is stirred for 2 hours at 20° and worked up in conventional manner (saturated NaCl solution/methylene chloride). Chromatography (ethyl acetate/hexane 80:20) gives 2-butyl-4,5-dihydro-5-(N,N-dimethylcarbamoylmethyl)-4-oxo-3-[2'-(1H-tetrazol-5-yl)biphenyl-4-ylmethyl]-3H-IP, m.p. 258°. K salt, monohydrate, m.p. 296°.

The following 2-butyl-4,5-dihydro-4-oxo-3-[2'-(1H-tetrazol-5-yl)biphenyl-4-ylmethyl]-5-$R^3$-3H-IP are obtained analogously from the 2'-cyanobiphenylyl compounds indicated under (a):
-5-cinnamyl-, m.p. 144°
-5-(3-ethoxycarbonyl-2-phenyl-2-propen-1-yl)-, m.p. 163°
-5-(α-methoxycarbonylbenzyl)-, m.p. 208°
-5-(2-methoxyimino-3,3-dimethylbutyl)-, m.p. 83°
-5-(2-oxo-3-m-tolyl-5-oxazolidinylmethyl)-, m.p. 206°
-5-carbamoylmethyl-
-5-(N-methylcarbamoylmethyl)-, m.p. 115°–116°
-5-(N-ethylcarbamoylmethyl)-
-5-(N-tert-butylcarbamoylmethyl)-, tetrahydrate, m.p. 212°
-5-(N,N-diethylcarbamoylmethyl)-, dihydrate, m.p. 255°
-5-(N,N-diisobutylcarbamoylmethyl)-, monohydrate, m.p. 180°
-5-(N-phenylcarbamoylmethyl)-, monohydrate, m.p. 227°
-5-(N-o-tolylcarbamoylmethyl)-, m.p. 163°
-5-(N-o-trifluoromethylphenylcarbamoylmethyl)-
-5-(N-o-ethoxycarbonylphenylcarbamoylmethyl)-, m.p. 190°
-5-(N-o-chlorophenylcarbamoylmethyl)-
-5-[N-(2,6-dimethylphenyl)carbamoylmethyl]-, pentahydrate, m.p. 247°
-5-[N-(2-pyridyl)carbamoylmethyl]-
-5-(N-methyl-N-phenylcarbamoylmethyl)-, m.p. 171°
-5-[N-methyl-N-(1,1-dimethyl-2-phenylethyl)carbamoylmethyl]-
-5-(N,N-diphenylcarbamoylmethyl)-, dihydrate, m.p. 212°
-5-(2-carbamoylethyl)-
-5-(2-N,N-dimethylcarbamoylethyl)-
-5-(2-N-phenylcarbamoylethyl)-
-5-[2-N-(2,6-dimethylphenyl)carbamoylethyl]-
-5-(3-nitro-2-oxo-propyl)-
-5-(6-BOC-amino-2-oxohexyl)-
-5-(N-ethoxycarbonylmethyl-N-methylcarbamoylmethyl)-
-5-(N-methylsulfonylcarbamoylmethyl)-
-5-(N-phenylsulfonylcarbamoylmethyl)-
-5-aziridinocarbonylmethyl-
-5-pyrrolidinocarbonylmethyl-, m.p. 215°
-5-piperidinocarbonylmethyl-
-5-(2-oxopyrrolidinocarbonylmethyl)-
-5-(2-oxopiperidinocarbonylmethyl)-
-5-(4-oxopiperidinocarbonylmethyl)-
-5-(4-o-methoxyphenylpiperidinocarbonylmethyl)-
-5-[4-(2-thienyl)piperidinocarbonylmethyl-
-5-(4-p-methoxybenzoylpiperidinocarbonylmethyl)-
-5-(2-ethoxycarbonylpyrrolidinocarbonylmethyl)-
-5-(3-ethoxycarbonylpiperidinocarbonylmethyl)-
-5-(3-hydroxymethyl-4-p-chlorophenylpiperidinocarbonylmethyl)-

-5-(3-N,N-diethylcarbamoylpiperidinocarbonylmethyl)-, m.p. 173°
-5-(3-acetamidopyrrolidinocarbonylmethyl)-
-5-morpholinocarbonylmethyl-
-5-(3-oxopiperazinocarbonylmethyl)-
-5-(4-methylpiperazinocarbonylmethyl)-
-5-(4-o-methoxyphenylpiperazinocarbonylmethyl)-
-5-(4-o-nitrophenylpiperazinocarbonylmethyl)-
-5-(3-ethoxycarbonylpiperazinocarbonylmethyl)-
-5-(4-BOC-piperazinocarbonylmethyl)-
-5-[4-(2-pyrimidinyl)piperazinocarbonylmethyl]-
-5-(4-p-fluorophenylsulfonylpiperazinocarbonylmethyl)-, m.p. 248°
-5-methylthiomethyl-
-5-methylsulfinylmethyl-
-5-methylsulfonylmethyl-
-5-phenylthiomethyl-
-5-phenylsulfinylmethyl-
-5-phenylsulfonylmethyl-
-5-(2-thienyl)thiomethyl-
-5-(2-pyridylaminosulfonylmethyl)-
-5-methoxysulfonylmethyl-.

EXAMPLE 8

(a) The 2-ethyl-3-(2'-cyanobiphenyl-4-ylmethyl)-4,5-dihydro-4-oxo-5-$R^3$-3H-IP below are obtained analogously to Example 7(a) from 2-ethyl-3-(2'-cyanobiphenyl-4-ylmethyl)-4,5-dihydro-4-oxo-3H-IP (m.p. 230°; obtainable from 2-ethyl-4,5-dihydro-4-oxo-1(or 3)H-IP with 4'-bromomethyl-2-cyanobiphenyl) and the compounds of the formula E—$R^3$ indicated in Example 7(b):
-5-cinnamyl-
-5-(3-ethoxycarbonyl-2-phenyl-2-propen-1-yl)-
-5-(α-methoxycarbonylbenzyl)-
-5-(2-methoxyimino-3,3-dimethylbutyl)-
-5-(2-oxo-3-m-tolyl-5-oxazolidinylmethyl)-
-5-carbamoylmethyl-
-5-(N-methylcarbamoylmethyl)-
-5-(N-ethylcarbamoylmethyl)-
-5-(N-tert-butylcarbamoylmethyl)-
-5-(N,N-dimethylcarbamoylmethyl)-, m.p. 234°
-5-(N,N-diethylcarbamoylmethyl)- m.p. 160°
-5-(N,N-diisobutylcarbamoylmethyl)-
-5-(N-phenylcarbamoylmethyl)-
-5-(N-o-tolylcarbamoylmethyl)-
-5-(N-o-trifluoromethylphenylcarbamoylmethyl)-
-5-(N-o-ethoxycarbonylphenylcarbamoylmethyl)-
-5-(N-o-chlorophenylcarbamoylmethyl)-
-5-[N-(2,6-dimethylphenyl)carbamoylmethyl]-
-5-[N-(2-pyridyl) carbamoylmethyl]-
-5-(N-methyl-N-phenylcarbamoylmethyl)-
-5-[N-methyl-N-(1,1-dimethyl-2-phenylethyl)carbamoylmethyl]-
-5-(N,N-diphenylcarbamoylmethyl)-
-5-(2-carbamoylethyl)-
-5-(2-N,N-dimethylcarbamoylethyl)-
-5-(2-N-phenylcarbamoylethyl)-
-5-[2-N-(2,6-dimethylphenyl)carbamoylethyl]-
-5-(3-nitro-2-oxopropyl)-
-5-(6-BOC-amino-2-oxohexyl)-
-5-(N-ethoxycarbonylmethyl-N-methylcarbamoylmethyl)-
-5-(N-methylsulfonylcarbamoylmethyl)-
-5-(N-phenylsulfonylcarbamoylmethyl)-
-5-aziridinocarbonyl-
-5-pyrrolidinocarbonylmethyl-
-5-piperidinocarbonylmethyl-, m.p. 221°
-5-(2-oxopyrrolidinocarbonylmethyl)-
-5-(2-oxopiperidinocarbonylmethyl)-
-5-(4-oxopiperidinocarbonylmethyl)-, m.p. 189°
-5-(4-o-methoxyphenylpiperidinocarbonylmethyl)-, m.p. 173°
-5-[4-(2-thienyl)piperidinocarbonylmethyl]-
-5-(4-p-methoxybenzoylpiperidinocarbonylmethyl)-
-5-(2-ethoxycarbonylpyrrolidinocarbonylmethyl)-
-5-(3-ethoxycarbonylpiperidinocarbonylmethyl)-
-5-(3hydroxymethyl-4-p-chlorophenylpiperidinocarbonylmethyl)-
-5-(3,N,N-diethylcarbamoylpiperidinocarbonylmethyl)-
-5-(3-acetamidopyrrolidinocarbonylmethyl)-, m.p. 153°
-5-morpholinocarbonylmethyl-, m.p. 214°
-5-(3-oxopiperazinocarbonylmethyl)-
-5-(4-methylpiperazinocarbonylmethyl)-
-5-(4-o-methoxyphenylpiperazinocarbonylmethyl)-, m.p. 156°
-5-(4-o-nitrophenylpiperazinocarbonylmethyl)-, m.p. 224°
-5-(3-ethoxycarbonylpiperazinocarbonylmethyl)-
-5-(4-BOC-piperazinocarbonylmethyl)-
-5-[4-(2-pyrimidinyl)piperazinocarbonylmethyl]-
-5-(4-p-fluorophenylsulfonylpiperazinocarbonylmethyl)-
-5-methylthiomethyl-
-5-methylsulfinylmethyl-
-5-methylsulfonylmethyl-
-5-phenylthiomethyl-
-5-phenylsulfinylmethyl-
-5-phenylsulfonylmethyl, m.p. 193°
-5-(2-thienyl)thiomethyl-
-5-(2-pyridylaminosulfonylmethyl)-
-5-methoxysulfonylmethyl-.

(b) The 2-ethyl-4,5-dihydro-4-oxo-3-[2'-(1H-tetrazol-5-yl)biphenyl-4-ylmethyl]-5-$R^3$-3H-IP below are obtained analogously to Example 7(b) from the 2'-cyanobiphenylyl compounds indicated under (a):
-5-cinnamyl-
-5-(3-ethoxycarbonyl-2-phenyl-2-propen-1-yl)-
-5-(α-methoxycarbonylbenzyl)-
-5-(2-methoxyimino-3,3-dimethylbutyl)-
-5-(2-oxo-3-m-tolyl-5-oxazolidinylmethyl)-
-5-carbamoylmethyl-
-5-(N-methylcarbamoylmethyl)-
-5-(N-ethylcarbamoylmethyl)-
-5-(N-tert-butylcarbamoylmethyl)-
-5-(N,N-dimethylcarbamoylmethyl)-, m.p. 182°
-5-(N,N-diethylcarbamoylmethyl)-, m.p. 192°
-5-(N,N-diisobutylcarbamoylmethyl)-
-5-(N-phenylcarbamoylmethyl)-
-5-(N-o-tolylcarbamoylmethyl)-
-5-(N-o-trifluoromethylphenylcarbamoylmethyl)-
-5-(N-o-ethoxycarbonylphenylcarbamoylmethyl)-
-5-(N-o-chlorophenylcarbamoylmethyl)[
-5-[N-(2,6-dimethylphenyl)carbamoylmethyl]-
-5-[N-(2-pyridyl)carbamoylmethyl]-
-5-(N-methyl-N-phenylcarbamoylmethyl)-
-5-[N-methyl-N-(1,1-dimethyl-2-phenylethyl)carbamoylmethyl]-
-5-(N,N-diphenylcarbamoylmethyl)-
-5-(2-carbamoylethyl)-
-5-(2-N,N-dimethylcarbamoylethyl)-
-5-(2-N-phenylcarbamoylethyl)-
-5-[2-N-(2,6-dimethylphenyl)carbamoylethyl]-
-5-(3-nitro-2-oxopropyl)-
-5-(6-BOC-amino-2-oxohexyl)-
-5-(N-ethoxycarbonylmethyl-N-methylcarbamoylmethyl)-
-5-(N-methylsulfonylcarbamoylmethyl)-

-5-(N-phenylsulfonylcarbamoylmethyl)-
-5-aziridinocarbonylmethyl-
-5-pyrrolidinocarbonylmethyl-
-5-piperidinocarbonylmethyl-, m.p. 200°
-5-(2-oxopyrrolidinocarbonylmethyl)-
-5-(2-oxopiperidinocarbonylmethyl)-
-5-(4-oxopiperidinocarbonylmethyl)-
-5-(4-o-methoxyphenylpiperidinocarbonylmethyl)-
-5-[4-(2-thienyl)piperidinocarbonylmethyl]-
-5-(4-p-methoxybenzoylpiperidinocarbonylmethyl)-
-5-(2-ethoxycarbonylpyrrolidinocarbonylmethyl)-
-5-(3-ethoxycarbonylpiperidinocarbonylmethyl)-
-5-(3-hydroxymethyl-4-p-chlorophenylpiperidinocarbonylmethyl)-
-5-(3-N,N-diethylcarbamoylpiperidinocarbonylmethyl)-
-5-(3-acetamidopyrrolidinocarbonylmethyl)-, m.p. 187°
-5-morpholinocarbonylmethyl-, m.p. 196°
-5-(3-oxopiperazinocarbonylmethyl)-
-5-(4-methylpiperazinocarbonylmethyl)-
-5-(4-o-methoxyphenylpiperazinocarbonylmethyl)-, m.p. 163°
-5-(4-o-nitrophenylpiperazinocarbonylmethyl)-, m.p. 223°
-5-(3-ethoxycarbonylpiperazinocarbonylmethyl)(
-5-(4-BOC-piperazinocarbonylmethyl)-
-5-[4-(2-pyrimidinyl)piperazinocarbonylmethyl]-
-5-(4-p-fluorophenylsulfonylpiperazinocarbonylmethyl)-
-5-methylthiomethyl-
-5-methylsulfinylmethyl-
-5-methylsulfonylmethyl-
-5-phenylthiomethyl-
-5-phenylsulfinylmethyl-
-5-phenylsulfonylmethyl-, m.p. 168°
-5-(2-thienyl)thiomethyl-
-5-(2-pyridylaminosulfonylmethyl)-
-5-methoxysulfonylmethyl-.

EXAMPLE 9

(a) The 2-cyclopropyl-3-(2'-cyanobiphenyl-4-ylmethyl)4,5-dihydro-4-oxo-5-$R^3$-3H-IP below are -obtained analogously to Example 7(a) from 2-cyclopropyl-3-(2'-cyanobiphenyl-4-methyl)-4,5-dihydro-4-oxo-3H-IP (m.p. 183°; obtainable from 2-cyclopropyl-4,5-dihydro-4-oxo-1(or 3)H-IP with 4'-bromomethyl-2-cyanobiphenyl) and the compounds of the formula E-$R^3$ indicated in Example 7(a):
-5-cinnamyl-
-5-(3-ethoxycarbonyl-2-phenyl-2-propen-1-yl)-
-5-(α-methoxycarbonylbenzyl)-
-5-(2-methoxyimino-3,3-dimethylbutyl)-
-5-(2-oxo-3-m-tolyl-5-oxazolidinylmethyl)-
-5-carbamoylmethyl-
-5-(N-methylcarbamoylmethyl)-
-5-(N-ethylcarbamoylmethyl)-
-5-(N-tert-butylcarbamoylmethyl)-
-5-(N,N-dimethylcarbamoylmethyl)-, Rf 0.16 (ethylacetate/methanol 9:1)
-5-(N,N-diethylcarbamoylmethyl)-
-5-(N,N-diisobutylcarbamoylmethyl)-
-5-(N-phenylcarbamoylmethyl)-
-5-(N-o-tolylcarbamoylmethyl)-
-5-(N-o-trifluoromethylphenylcarbamoylmethyl)-
-5-(N-o-ethoxycarbonylphenylcarbamoylmethyl)-
-5-(N-o-chlorophenylcarbamoylmethyl)[
-5-[N-(2,6-dimethylphenyl)carbamoylmethyl]-
-5-[N-(2-pyridyl)carbamoylmethyl]-
-5-(N-methyl-N-phenylcarbamoylmethyl)-
-5-[N-methyl-N-(1,1-dimethyl-2-phenylethyl)carbamoylmethyl]-
-5-(N,N-diphenylcarbamoylmethyl)-, Rf 0.39 (ethylacetate/methanol 9:1)
-5-(2-carbamoylethyl)-
-5-(2-N,N-dimethylcarbamoylethyl)-
-5-(2-N-phenylcarbamoylethyl)-
-5-[2-N-(2,6-dimethylphenyl)carbamoylethyl]-
-5-(3-nitro-2-oxopropyl)-
-5-(6-BOC-amino-2-oxohexyl)-
-5-(N-ethoxycarbonylmethyl-N-methylcarbamoylmethyl)-
-5-(N-methylsulfonylcarbamoylmethyl)-
-5-(N-phenylsulfonylcarbamoylmethyl)-
-5-aziridinocarbonylmethyl-
-5-pyrrolidinocarbonylmethyl-
-5-piperidinocarbonylmethyl-
-5-(2-oxopyrrolidinocarbonylmethyl)-
-5-(2-oxopiperidinocarbonylmethyl)-
-5-(4-oxopiperidinocarbonylmethyl)-
-5-(4-o-methoxyphenylpiperidinocarbonylmethyl)-
-5-[4-(2-thienyl)piperidinocarbonylmethyl]-
-5-(4-p-methoxybenzoylpiperidinocarbonylmethyl)-
-5-(2-ethoxycarbonylpyrrolidinocarbonylmethyl)-
-5-(3-ethoxycarbonylpiperidinocarbonylmethyl)-
-5-(3-hydroxymethyl-4-p-chlorophenylpiperidinocarbonylmethyl)-
-5-(3-N,N-diethylcarbamoylpiperidinocarbonylmethyl)-
-5-(3-acetamidopyrrolidinocarbonylmethyl)-
-5-morpholinocarbonylmethyl-
-5-(3-oxopiperazinocarbonylmethyl)-
-5-(4-methylpiperazinocarbonylmethyl)-
-5-(4-o-methoxyphenylpiperazinocarbonylmethyl)-
-5-(4-o-nitrophenylpiperazinocarbonylmethyl)-
-5-(3-ethoxycarbonylpiperazinocarbonylmethyl)-
-5-(4-BOC-piperazinocarbonylmethyl)-
-5-[4-(2-pyrimidinyl)piperazinocarbonylmethyl]-
-5-(4-p-fluorophenylsulfonylpiperazinocarbonylmethyl)-
-5-methylthiomethyl-
-5-methylsulfinylmethyl-
-5-methylsulfonylmethyl-
-5-phenylthiomethyl-
-5-phenylsulfinylmethyl-
-5-phenylsulfonylmethyl-
-5-(2-thienyl)thiomethyl-
-5-(2-pyridylaminosulfonylmethyl)-
-5-methoxysulfonylmethyl-.

(b) The 2-cyclopropyl-4,5-dihydro-4-oxo-3-[2'-(1H-tetrazol-5yl)biphenyl-4-ylmethyl]-5-$R^3$-3H-IP below are obtained analogously to Example 7(b) from the 2'-cyanobiphenylyl compounds indicated under (a):
-5-cinnamyl-
-5-(3-ethoxycarbonyl-2-phenyl-2-propen-1-yl)-
-5-(α-methoxycarbonylbenzyl)-
-5-(2-methoxyimino-3,3-dimethylbutyl)-
-5-(2-oxo-3-m-tolyl-5-oxazolidinylmethyl)-
-5-carbamoylmethyl-
-5-(N-methylcarbamoylmethyl)-
-5-(N-ethylcarbamoylmethyl)-
-5-(N-tert-butylcarbamoylmethyl)-
-5-(N,N-dimethylcarbamoylmethyl)-, m.p. 231°
-5-(N,N-diethylcarbamoylmethyl)-
-5-(N,N-diisobutylcarbamoylmethyl)-
-5-(N-phenylcarbamoylmethyl)-
-5-(N-o-tolylcarbamoylmethyl)-
-5-(N-o-chlorophenylcarbamoylmethyl)-
-5-[N-(2,6-dimethylphenyl)carbamoylmethyl]-
-5-[N-(2-pyridyl)carbamoylmethyl]-
-5-(N-methyl-N-phenylcarbamoylmethyl)-
-5-[N-methyl-N-(1,1-dimethyl-2-phenylethyl)carbamoylmethyl]-

-5-(N,N-diphenylcarbamoylmethyl)-, m.p. 204°
-5-(2-carbamoylethyl)-
-5-(2-N,N-dimethylcarbamoylethyl)-
-5-(2-N-phenylcarbamoylethyl)-
-5-[2-N-(2,6-dimethylphenyl)-carbamoylethyl]-
-5-(3-nitro-2-oxopropyl)-
-5-(6-BOC-amino-2-oxohexyl)-
-5-(N-ethoxycarbonylmethyl-N-methylcarbamoylmethyl)-
-5-(N-methylsulfonylcarbamoylmethyl)-
-5-(N-phenylsulfonylcarbamoylmethyl)-
-5-aziridinocarbonylmethyl-
-5-pyrrolidinocarbonylmethyl-
-5-piperidinocarbonylmethyl-
-5-(2-oxopyrrolidinocarbonylmethyl)-
-5-(2-oxopiperidinocarbonylmethyl)-
-5-(4-oxopiperidinocarbonylmethyl)-
-5-(4-o-methoxyphenylpiperidinocarbonylmethyl)-
-5-[4-(2-thienyl)piperidinocarbonylmethyl]-
-5-(4-p-methoxybenzoylpiperidinocarbonylmethyl)-
-5-(2-ethoxycarbonylpyrrolidinocarbonylmethyl)-
-5-(3-ethoxycarbonylpiperidinocarbonylmethyl)-
-5-(3-hydroxymethyl-4-p-chlorophenylpiperidinocarbonylmethyl)-
-5-(3-N,N-diethylcarbamoylpiperidinocarbonylmethyl)-
-5-(3-acetamidopyrrolidinocarbonylmethyl)-
-5-morpholinocarbonylmethyl-
-5-(3-oxopiperazinocarbonylmethyl)-
-5-(4-methylpiperazinocarbonylmethyl)-
-5-(4-o-methoxyphenylpiperazinocarbonylmethyl)-
-5-(4-o-nitrophenylpiperazinocarbonylmethyl)-
-5-(3-ethoxycarbonylpiperazinocarbonylmethyl)-
-5-(4-BOC-piperazinocarbonylmethyl)-
-5-[4-(2-pyrimidinyl)piperazinocarbonylmethyl]-
-5-(4-p-fluorophenylsulfonylpiperazinocarbonylmethyl)-
-5-methylthiomethyl-
-5-methylsulfinylmethyl-
-5-methylsulfonylmethyl-
-5-phenylthiomethyl-
-5-phenylsulfinylmethyl-
-5-phenylsulfonylmethyl-
-5-(2-thienyl)thiomethyl-
-5-(2-pyridylaminosulfonylmethyl)-
-5-methoxysulfonylmethyl-.

EXAMPLE 10

(a) 2-Butyl-4,5-dihydro-5-(N,N-dimethylcarbamoylmethyl)-4-oxo-3-[2'-(2-triphenylmethyl-2H-tetrazol-5-yl)biphenyl-4-ylmethyl]-3H-IP, m.p. 187°, is obtained analogously to Example 7(a) from 2-butyl-4,5-dihydro-4-oxo-3-[2'-(2-triphenylmethyl-2H-tetrazol-5-yl)biphenyl-4-ylmethyl]-3H-IP with N,N-dimethylchloroacetamide.

The following 2-butyl-4,5-dihydro-4-oxo-3-[2'-(2-triphenylmethyl-2H-tetrazol-5-yl)biphenyl-4-ylmethyl]-5 -$R^3$-3H-IP are obtained analogously with the compounds of formula E—$R^3$ indicated in Example 7(a):
-5-cinnamyl-, m.p. 89°
-5-(3-ethoxycarbonyl-2-phenyl-2-propen-1-yl)-, m.p. 89°
-5-(α-methoxycarbonylbenzyl)-, m.p. 94°
-5-(2-methoxyimino-3,3-dimethylbutyl)-
-5-(2-oxo-3-m-tolyl-5-oxazolidinylmethyl)-, m.p. 107°
-5-carbamoylmethyl-
-5-(N-methylcarbamoylmethyl)-
-5-(N-ethylcarbamoylmethyl)-
-5-(N-tert-butylcarbamoylmethyl)-
-5-(N,N-diethylcarbamoylmethyl)-
-5-(N,N-diisobutylcarbamoylmethyl)-
-5-(N-phenylcarbamoylmethyl)-
-5-(N-o-tolylcarbamoylmethyl)-
-5-(N-o-trifluoromethylphenylcarbamoylmethyl)-
-5-(N-o-ethoxycarbonylphenylcarbamoylmethyl)-
-5-(N-o-chlorophenylcarbamoylmethyl)-
-5-[N-(2,6-dimethylphenyl)carbamoylmethyl]-
-5-[N-(2-pyridyl)carbamoylmethyl]-
-5-(N-methyl-N-phenylcarbamoylmethyl)-
-5-[N-methyl-N-(1,1-dimethyl-2-phenylethyl)carbamoylmethyl]-
-5-(N,N-diphenylcarbamoylmethyl)-
-5-(2-carbamoylethyl)-
-5-(2-N,N-dimethylcarbamoylethyl)-
-5-(2,N-phenylcarbamoylethyl)-
-5-[2-N-(2,6-dimethylphenyl)carbamoylethyl]-
-5-(3-nitro-2-oxopropyl)-
-5-(6-BOC-amino-2-oxohexyl)-
-5-(N-ethoxycarbonylmethyl-N-methylcarbamoylmethyl)-
-5-(N-methylsulfonylcarbamoylmethyl)-
-5-(N-phenylsulfonylcarbamoylmethyl)-
-5-aziridinocarbonylmethyl-
-5-pyrrolidinocarbonylmethyl-
-5-piperidinocarbonylmethyl-
-5-(2-oxopyrrolidinocarbonylmethyl)-
-5-(2-oxopiperidinocarbonylmethyl)-
-5-(4-oxopiperidinocarbonylmethyl)-
-5-(4-o-methoxyphenylpiperidinocarbonylmethyl)-
-5-[4-(2-thienyl)piperidinocarbonylmethyl]-
-5-(4-p-methoxybenzoylpiperidinocarbonylmethyl)-
-5-(2-ethoxycarbonylpyrrolidinocarbonylmethyl)-
-5-(3-ethoxycarbonylpiperidinocarbonylmethyl)-
-5-(3-hydroxymethyl-4-p-chlorophenylpiperidinocarbonylmethyl)-
-5-(3-N,N-diethylcarbamoylpiperidinocarbonylmethyl)-
-5-(3-acetamidopyrrolidinocarbonylmethyl)-
-5-morpholinocarbonylmethyl-
-5-(3-oxopiperazinocarbonylmethyl)-
-5-(4-methylpiperazinocarbonylmethyl)-
-5-(4-o-methoxyphenylpiperazinocarbonylmethyl)-
-5-(4-o-nitrophenylpiperazinocarbonylmethyl)-
-5-(3-ethoxycarbonylpiperazinocarbonylmethyl)-
-5-(4-BOC-piperazinocarbonylmethyl)-
-5-[4-(2-pyrimidinyl)piperazinocarbonylmethyl]-
-5-(4-p-fluorophenylsulfonylpiperazinocarbonylmethyl)-
-5-methylthiomethyl-
-5-methylsulfinylmethyl-
-5-methylsulfonylmethyl-
-5-phenylthiomethyl-
-5-phenylsulfinylmethyl-
-5-phenylsulfonylmethyl-
-5-(2-thienyl)thiomethyl-
-5-(2-pyridylaminosulfonylmethyl)-
-5-methoxysulfonylmethyl-
and the 2-ethyl-4,5-dihydro-4-oxo-3-[2'-(2-triphenylmethyl-2H-tetrazol-5-yl)biphenyl-4-ylmethyl]-5-$R^3$-3H-IP below:
-5-cinnamyl-
-5-(3-ethoxycarbonyl-2-phenyl-2-propen-1-yl)-
-5-(α-methoxycarbonylbenzyl)-
-5-(2-methoxyimino-3,3-dimethylbutyl)-
-5-(2-oxo-3-m-tolyl-5-oxazolidinylmethyl)-
-5-carbamoylmethyl-
-5-(N-methylcarbamoylmethyl)-
-5-(N-ethylcarbamoylmethyl)-
-5-(N-tert-butylcarbamoylmethyl)
-5-(N,N-dimethylcarbamoylmethyl)
-5-(N,N-diethylcarbamoylmethyl)-
-5-(N,N-diisobutylcarbamoylmethyl)-

-5-(N-phenylcarbamoylmethyl)-
-5-(N-o-tolylcarbamoylmethyl)-
-5-(N-o-trifluoromethylphenylcarbamoylmethyl)-
-5-(N-o-ethoxycarbonylphenylcarbamoylmethyl)-
-5-(N-o-chlorophenylcarbamoylmethyl)-
-5-[N-(2,6-dimethylphenyl)carbamoylmethyl]-
-5-[N-(2-pyridyl)carbamoylmethyl]-
-5-(N-methyl-N-phenylcarbamoylmethyl)-
-5-[N-methyl-N-(1,1-dimethyl-2-phenylethyl)carbamoylmethyl]-
-5-(N,N-diphenylcarbamoylmethyl)-
-5-(2-carbamoylethyl)-
-5-(2-N,N-dimethylcarbamoylethyl)-
-5-(2-N-phenylcarbamoylethyl)-
-5-[2-N-(2,6-dimethylphenyl)carbamoylethyl]-
-5-(3-nitro-2-oxopropyl)-
-5-(6-BOC-amino-2-oxohexyl)-
-5-(N-ethoxycarbonylmethyl-N-methylcarbamoylmethyl)-
-5-(N-methylsulfonylcarbamoylmethyl)-
-5-(N-phenylsulfonylcarbamoylmethyl)-
-5-aziridinocarbonylmethyl-
-5-pyrrolidinocarbonylmethyl-
-5-piperidinocarbonylmethyl-
-5-(2-oxopyrrolidinocarbonylmethyl)-
-5-(2-oxopiperidinocarbonylmethyl)-
-5-(4-oxopiperidinocarbonylmethyl)-
-5-(4-o-methoxyphenylpiperidinocarbonylmethyl)-
-5-[4-(2-thienyl)piperidinocarbonylmethyl]-
-5-(4-p-methoxybenzoylpiperidinocarbonylmethyl)-
-5-(2-ethoxycarbonylpyrrolidinocarbonylmethyl)-
-5-(3-ethoxycarbonylpiperidinocarbonylmethyl)-
-5-(3-hydroxymethyl-4-p-chlorophenylpiperidinocarbonylmethyl)-
-5-(3,N,N-diethylcarbamoylpiperidinocarbonylmethyl)-
-5-(3-acetamidopyrrolidinocarbonylmethyl)-
-5-morpholinocarbonylmethyl-
-5-(3-oxopiperazinocarbonylmethyl)-
-5-(4-methylpiperazinocarbonylmethyl)-
-5-(4-o-methoxyphenylpiperazinocarbonylmethyl)-
-5-(4-o-nitrophenylpiperazinocarbonylmethyl)-
-5-(3-ethoxycarbonylpiperazinocarbonylmethyl)-
-5-(4-BOC-piperazinocarbonylmethyl)-
-5-[4-(2-pyrimidinyl)piperazinocarbonylmethyl]-
-5-(4-p-fluorophenylsulfonylpiperazinocarbonylmethyl)-
-5-methylthiomethyl-
-5-methylsulfinylmethyl-
-5-methylsulfonylmethyl-
-5-phenylthiomethyl-
-5-phenylsulfinylmethyl-
-5-phenylsulfonylmethyl-
-5-(2-thienyl)thiomethyl-
-5-(2-pyridylaminosulfonylmethyl)-
-5-methoxysulfonylmethyl-.

(b) The product obtained according to (a) (1 g) is dissolved in 60 ml of 4N HCl in dioxane and the solution is stirred for 16 hours at 20°. It is evaporated and worked up in conventional manner to give 2-butyl-4,5-dihydro-5-(N,N-dimethylcarbamoylmethyl)-4-oxo-3-[2'-(1H-tetrazol-5-yl)biphenyl-4-ylmethyl]-3H-IP, m.p. 258°.

The 1H-tetrazol-5-yl compounds indicated in Examples 7(b) and 8(b) are obtained analogously from the corresponding 2-triphenylmethyl-2H-tetrazol-5-yl compounds indicated under (a).

EXAMPLE 11

2-Butyl-3-(p-2-cyano-2-phenylvinylbenzyl)-4,5-dihydro-5-(N,N-dimethylcarbamoylmethyl)-4-oxo-3H-IP is obtained analogously to Example 7(a) from 2-butyl-3-(p-2-cyano-2-phenylvinylbenzyl)-4,5-dihydro-4-oxo-3H-IP (m.p. 160°; obtainable from 2-butyl-4,5-dihydro-4-oxo-1(or 3)H-IP and 3-p-bromomethylphenyl-2-phenylacrylonitrile) with N,N-dimethylchloroacetamide.

EXAMPLE 12

210 mg of DCCI are added to a solution of 0.44 g of 2-butyl-3-(2'-cyanobiphenyl-4-ylmethyl)-4,5-dihydro-4-oxo-3H-IP-5-acetic acid ["B"; m.p. 222°; obtainable by reaction of 2-butyl-3-(2'-cyanobiphenyl-4-ylmethyl)-4,5-dihydro-4-oxo-3H-IP with ethyl bromoacetate to give the 5-ethoxycarbonylmethyl derivative (m.p. 152°) and subsequent hydrolysis] in 14 ml of THF, the mixture is stirred at 20° for 10 min, 72 mg of pyrrolidine are added and the mixture is stirred at 20° for a further 18 hours. It is filtered, the filtrate is worked up in the customary manner, the crude product is chromatographed on silica gel (ethyl acetate/methanol 80:20) and 2-butyl-3-(2'-cyanobiphenyl-4-ylmethyl)-4,5-dihydro-4-oxopyrrolidinocarbonylmethyl- 3H-IP, m.p. 166°, is obtained.

EXAMPLE 13

1.94 g of DAPECI, 1.36 g of 1-hydroxybenzotriazole and 1.1 ml of N-methylmorpholine are added successively to a solution of 4.4 g of "B" and 2.44 g of 1-p-fluorophenylsulfonylpiperazine in 90 ml of DMF, the mixture is stirred at 20° for 5 hours, the product is precipitated with water, filtered off, washed with water and dried, and 2-butyl-3-(2'-cyanobiphenyl-4-ylmethyl)-4,5-dihydro-4-oxo-5-(4-p-fluorophenylsulfonylpiperazinocarbonylmethyl)-3H-IP, m.p. 207°, are obtained.

EXAMPLE 14

A solution of 4.4 g of "B" in 20 ml of THF is added dropwise with stirring to a solution of 1.6 g of 1,1'-carbonyldiimidazole in 20 ml of THF and the mixture is then heated for 30 min. After cooling, 1.6 g of benzenesulfonamide are added, the mixture is stirred for 10 min, a solution of 1.48 g of 1,8-diazabicyclo[5,4,0]-undec-7-ene in 10 ml of THF is added, the mixture is stirred at 20° for 18 hours and worked up in the customary manner (1N hydrochloric acid/dichloromethane) and 2-butyl-3-(2'-cyanobiphenyl-4-ylmethyl)-4,5-dihydro-4-oxo-5-(N-phenylsulfonylcarbamoylmethyl)-3H-IP, m.p. 193°, is obtained.

EXAMPLE 15

2-Ethyl-3-(2'-cyanobiphenyl-4-ylmethyl)-4,5-dihydro-4-oxo-5-(N-N-diethylcarbamoylmethyl)-3H-IP, m.p. 160°, is obtained analogously to Example 12 from 2-ethyl-3-(2'-cyanobiphenyl-4-ylmethyl)-4,5-dihydro-4-oxo-3H-IP-5-acetic acid [m.p. 221°; obtainable by reaction of 2-ethyl-3-(2'-cyanobiphenyl-4-ylmethyl)-4,5-dihydro-4-oxo-3H-IP with ethyl bromoacetate to give 2-ethyl-3-(2'-cyanobiphenyl-4-ylmethyl)-4,5-dihydro-4-oxo-5-ethoxycarbonylmethyl-3H-IP (m.p. 143°) and subsequent hydrolysis] and diethylamine in the presence of DCCI.

EXAMPLE 16

The 2-butyl-4,5-dihydro-4-oxo-3-[2'-(1H-tetrazo-1-5-yl)biphenyl-4-ylmethyl]-5-$R^3$-3H-IP below are obtained analogously to Example 1(b) by hydrolysis of the corresponding ethyl esters indicated in Example 7 (b):
-5-(3-carboxy-2-phenyl-2-propen-1-yl)-

-5-(N-o-carboxyphenylcarbamoylmethyl)-.

EXAMPLE 17

A solution of 1 g of 2-butyl-4,5-dihydro-5-(3-nitro-2-oxopropyl)-4-oxo-3-[2'-(1H-tetrazol-5-yl)biphenyl-4-ylmethyl]-3H-IP in 20 ml of methanol is hydrogenated on 0.3 g of 5% Pd-on-charcoal at 20° and normal pressure until the calculated amount of $H_2$ has been taken up. The catalyst is filtered off and the filtrate is evaporated to give 5-(3-amino-2-oxopropyl)-2-butyl-4,5-dihydro-4-oxo-3-[2'-(1H-tetrazol-5-yl)biphenyl-4-ylmethyl]-3H-IP.

EXAMPLE 18

A solution of 1 g of 5-(6-BOC-amino-2-oxohexyl)-2-butyl-4,5-dihydro-4-oxo-3-[2'-(1H-tetrazol-5-yl)biphenyl-4-ylmethyl]-3H-IP in 20 ml of dichloromethane and 20 ml of trifluoroacetic acid is stirred at 20° for 1 hour, evaporated and worked up in conventional manner. 5-(6-amino-2-oxohexyl)-2-butyl-4,5-dihydro-4-oxo-3-[2'-(1H-tetrazol-5-yl)biphenyl-4-ylmethyl]-3H-IP is obtained.

The 2-ethyl- or the 2-butyl-4,5-dihydro-4-oxo-3-[2'-(1H-tetrazol-5-yl)biphenyl-4-ylmethyl]-5-(4-piperazinocarbonylmethyl)-3H-IP is obtained analogously from 2-ethyl- or from 2-butyl-4,5-dihydro-4-oxo-3-[2'-(1H-tetrazol-5-yl)biphenyl-4-ylmethyl]-5-(4-BOC-piperazinocarbonylmethyl)-3H-IP.

EXAMPLE 19

A mixture of 7.67 g of 2-butyl-4,5-dihydro-5-(3,3-dimethyl-2-oxobutyl)-3-[2'-(2-triphenylmethyl-2H-tetrazol-5-yl)biphenyl-4-ylmethyl]-3H-IP, 1.67 g of o-methylhydroxylamine hydrochloride, 200 ml of methanol and 3.2 g of pyridine is stirred at 20° for 72 hours. 2-butyl-4,5-dihydro-5-(3,3-dimethyl-2-oxobutyl)-3-[2'-(1H-tetrazol-5-yl)biphenyl-4-ylmethyl]-3H-IP is formed as an intermediate which is not isolated. After conventional working up (chromatography on silica gel using ethyl acetate/methanol), 2-butyl-4,5-dihydro-5-(3,3-dimethyl-2-methoxyiminobutyl)-3-[2'-(1H-tetrazol-5-yl)biphenyl-4-ylmethyl]-3H-IP, is obtained, m.p. 83°.

The following examples relate to pharmaceutical formulations containing active ingredients of formula I or their salts.

Example A: Tablets and coated tablets

Tablets of the following composition are produced by compression in conventional manner and, where required, are provided with a conventional sucrose-based coating:

Active ingredient of formula I 100 mg
Microcrystalline cellulose 278.8 mg
Lactose 110 mg
Maize starch 11 mg
Magnesium stearate 5 mg
Finely divided silicon dioxide 0.2 mg

Example B: Hard gelatin capsules

Conventional two-part hard gelatin capsules are each filled with
Active ingredient of formula I 100 mg
Lactose 150 mg
Cellulose 50 mg
Magnesium stearate 6 mg

Example C: Soft gelatin capsules

Conventional soft gelatin capsules are filled with a mixture of 50 mg of active ingredient and 250 mg of olive oil in each case.

Example D: Ampoules

A solution of 200 g of active ingredient in 2 kg of propane-1,2-diol is made up to 10 l with water and filled into ampoules so that each ampoule contains 20 mg of active ingredient.

Example E: Aqueous suspension for oral administration

An aqueous suspension of the active ingredient is prepared in conventional manner. The unit dose (5 ml) contains 100 mg of active ingredient, 100 mg of Na carboxymethylcellulose, 5 mg of Na benzoate and 100 mg of sorbitol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazopyridine compound of formula I:

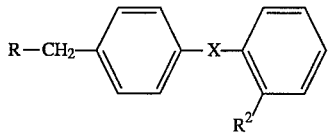

wherein
R is

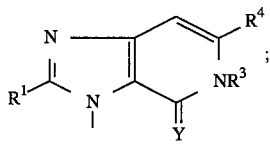

$R^1$ is A or $C_3$–$C_7$—cycloalkyl—;

$R^2$ is CN or 1H-tetrazol-5-yl;

$R^3$ is alkenyl having 2–6 C atoms in the alkenyl moiety and which is substituted by Ar or is substituted by Ar and COOA, or is —$C_nH_{2n}$—$R^9$ or —$CHR^{10}$—$C_kH_{2k}$—$R^{11}$;

$R^4$ is H;

$R^6$ and $R^7$ are each, independently, H, A, Ar or $ArC_nH_{2n}$—;

$R^6$ can also be —$CH_2COOA$; or $R^6$ and $R^7$ together can also be an alkylene chain having 2–5 C atoms, which can be monosubstituted by carbonyl oxygen, Ar, —COOA, —CO—N(A)$_2$ or —NH—CO—A or interrupted by O or by —$NR^{16}$—;

$R^9$ is $Het^1$, —CO—$NR^6R^7$, —C(=$NR^{12}$)—A or —S(O)$_m$—Ar;

29

$R^{10}$ is COOH or COOA;
$R^{11}$ is Ar;
$R^{12}$ is $OR^{13}$;
$R^{13}$ is A;
$R^{16}$ is Ar or $SO_2$—Ar;
X is absent;
Y is O;
A is alkyl having 1–6 C atoms;
Ar is an unsubstituted phenyl group or a phenyl group monosubstituted or disubstituted by A, $CF_3$, OA, COOA or Hal;
$Het^1$ is 2-oxo-3-Ar-5-oxazolidinyl;
Hal is F, Cl, Br or I;
k is 0, 1, 2, 3 or 4;
m is 0, 1 or 2; and
n is 1, 2, 3, 4, 5 or 6; or a pharmaceutically acceptable salt thereof.

2. A method of treating of hypertension, cardiac insufficiency, hypertrophy of the blood vessels and of the heart, hyperplasia of the blood vessels and of the heart, angina pectoris, or cardiac infarct, comprising administering a compound according to claim 1.

3. A method according to claim 2, wherein said compound is administered in a daily dosage of 0.1–100 mg/kg of body weight.

4. A compound according to claim 1, wherein $R^1$ is ethyl, propyl, butyl or cyclopropyl.

5. A compound according to claim 1, wherein $R^3$ is —$C_nH_{2n}$—CO—$NR^6R^7$ or —$C_nH_{2n}$—$S(O)_m$—Ar.

6. A compound according to claim 5, wherein $R^3$ is —$CH_2$—CO—$NR^6R^7$ or —$CH_2$—$S(O)_m$—Ar.

7. A compound according to claim 1, wherein $R^3$ is —$CHR^{10}$—$R^{11}$.

8. A compound according to claim 1, wherein $R^3$ is —$CHR^{10}$—$CH_2$—$R^{11}$.

9. A compound according to claim 1, wherein $R^3$ is alkenyl having 2–6 C atoms substituted by COOA and substituted by Ar.

10. A compound according to claim 1, wherein
$R^1$ is A;
$R^6$ and $R^7$ are each, independently, H, A, Ar or $ArC_nH_{2n}$—;
$R^9$ is $Het^1$, —CO—$NR^6R^7$ or —C(=$NR^{12}$)—A; and
k is 1, 2, 3 or 4.

11. A compound of claim 1, wherein said compound is:
(a) 2-butyl-5-cinnamyl-4,5-dihydro-4-oxo-3-[2'-(1H-tetrazol-5-yl)biphenyl-4-ylmethyl]-3H-imidazo[4,5-c]pyridine or a pharmaceutically acceptable salt thereof;

30

(b) 2-butyl-5-(3-ethoxycarbonyl-2-phenyl-2-propen-1-yl)-4,5-dihydro-4-oxo-3-[2'-(1H-tetrazol-5-yl)biphenylyl-4-methyl]-3H-imidazo[4,5-c]pyridine or a pharmaceutically acceptable salt thereof;

(c) 2-butyl-4,5-dihydro-5-(N,N-dimethylcarbamoylmethyl)-4-oxo-3-[2'-(1H-tetrazol-5-yl)biphenyl-4-ylmethyl]-3H-imidazo[4,5-c]pyridine or a pharmaceutically acceptable salt thereof, (d) 2-butyl-4,5-dihydro-5-α-methoxycarbonylbenzyl-4-oxo-3-[2'-(1H-tetrazol-5-yl)biphenyl-4-ylmethyl]3H-imidazo[4,5-c]pyridine or a pharmaceutically acceptable salt thereof;

(e) 2-butyl-4,5-dihydro-5-(2methoxyimino-3,3-dimethylbutyl)-4-oxo-3-[2'-(1H-tetrazol-5-yl)biphenyl-4-ylmethyl]-3H-imidazo[4,5-c]pyridine or a pharmaceutically acceptable salt thereof; or (f) 2-butyl-4,5-dihydro-4-oxo-5-(2-oxo-3-m-tolyl-5-oxazolidinylmethyl)-3-[2'-(1H-tetrazol5-yl)biphenyl-4-ylmethyl]-3H-imidazo[4,5-c]pyridine or a pharmaceutically acceptable salt thereof.

12. A compound according to claim 1, wherein $R^2$ is 1H-tetrazol-5-yl.

13. A compound according to claim 1, wherein $R^1$ is alkyl having 3–6 C atoms.

14. A compound according to claim 1, wherein R is a 2-butyl-4,5-dihydro-4-oxo-5-$R^3$-3H-imidazo[4,5-c]pyridin-3-yl radical; $R^2$ is 1H-tetrazol-5-yl; and $R^3$ is —$C_nH_{2n}$—$CONR^6R^7$ and X is absent.

15. A pharmaceutical composition comprising a compound according to claim 1 and a physiologically acceptable carrier.

16. A pharmaceutical composition according to claim 15, wherein said compound is present in an amount of 1 mg–1 g.

17. A method of treating of angiotensin(II)-dependent hypertension or angiotensin(II)-dependent cardiac insufficiency, comprising administering a compound according to claim 1.

18. A method according to claim 17, wherein said compound is administered in a daily dosage of 0.1–100 mg/kg of body weight.

19. A method according to claim 17, wherein said disease is angiotensin(II)-dependent hypertension.

20. A method according to claim 18, wherein said disease is angiotensin(II)-dependent hypertension.

* * * * *